United States Patent [19]

Cross et al.

[11] Patent Number: 4,959,366

[45] Date of Patent: Sep. 25, 1990

[54] ANTI-ARRHYTHMIC AGENTS

[75] Inventors: Peter E.Cross, Geoffrey N. Thomas, John E. Arrowsmith, all of New York, N.Y.

[73] Assignee: Pfizer Inc., New York, N.Y.

[21] Appl. No.: 44,086

[22] Filed: Apr. 29, 1987

[30] Foreign Application Priority Data

May 1, 1986 [GB] United Kingdom ................. 8610668
Dec. 17, 1986 [IE] Ireland ................................ 8630059

[51] Int. Cl.$^5$ ..................... C07C 143/75; C07C 93/06
[52] U.S. Cl. .................. 514/239.5; 514/255; 514/315; 514/410; 514/605; 514/618; 514/619; 514/620; 514/621; 514/649; 514/651; 514/654; 544/165; 544/167; 544/399; 546/226; 546/539; 564/99; 564/162; 564/164; 564/166; 564/336; 564/341; 564/348; 564/354
[58] Field of Search ................. 564/99, 336, 341, 348, 564/354, 162, 164, 166; 514/605, 821, 239.5, 255, 315, 410, 618, 619, 620, 621; 546/226; 548/539; 544/399, 165, 167

[56] References Cited

U.S. PATENT DOCUMENTS

| | | | |
|---|---|---|---|
| 3,341,584 | 9/1967 | Larsen et al. | 260/556 |
| 3,478,149 | 11/1969 | Larsen et al. | 424/228 |
| 3,574,741 | 4/1971 | Gould et al. | 260/556 |
| 3,660,487 | 5/1972 | Larsen et al. | 260/556 |
| 3,758,692 | 9/1973 | Larsen et al. | 424/321 |
| 3,852,468 | 12/1974 | Howe et al. | 564/99 |
| 4,396,627 | 8/1983 | Ainsworth et al. | 564/99 |
| 4,478,849 | 10/1984 | Ainsworth et al. | 564/99 |

FOREIGN PATENT DOCUMENTS

| | | | |
|---|---|---|---|
| 0164865 | 12/1985 | European Pat. Off. | 514/605 |
| 977261 | 7/1966 | France | 514/605 |
| 1263987 | 2/1972 | United Kingdom | 514/605 |
| 1301134 | 12/1982 | United Kingdom | 514/605 |
| 2135883 | 9/1984 | United Kingdom | 514/605 |

OTHER PUBLICATIONS

Larsen et al., "Sulfonanilides, II Anbalogs of Catecholamines", J. Am. Chem. Soc. 75, 4334 (1953).

*Primary Examiner*—Richard L. Raymond
*Assistant Examiner*—Raymond Covington
*Attorney, Agent, or Firm*—Peter C. Richardson; Paul H. Ginsburg; Robert F. Sheyka

[57] ABSTRACT

A series of [N-alkyl-N-(nitro-, alkylsulphonamido, or amino-phenalkyl)amino]-alkyl, alkoxy or alkylthio phenyl derivatives having utility as anti-arrhythmic agents.

48 Claims, No Drawings

ANTI-ARRHYTHMIC AGENTS

BACKGROUND OF THE INVENTION

This invention relates to certain sulfonamides which are antiarrhythmic agents, and to intermadiates therefor.

The antiarrhythmic compounds of the invention prolong the duration of the action potential in cardiac muscle and conducting tissue, and thereby increase refractoriness to premature stimuli. Thus, they are Class III antiarrhythmic agents according to the classification of Vaughan Williams (Anti-Arrhythmic Action, E. M. Vaughan Williams, Academic Press, 1980). They are effective in atria, ventricles and conducting tissue both in vitro and in vivo and are therefore useful for the prevention and treatment of a wide variety of ventricular and supraventricular arrhythmias including atrial and ventricular fibrillation. Because they do not alter the speed at which impulses are conducted, they have less propensity than current drugs (mostly Class 1) to precipitate or aggravate arrhythmias, and also produce less neurological side effects. Some of the compounds also have some positive inotropic activity and therefore are particularly beneficial in patients with impaired cardiac pump function.

Thus the invention provides compounds of the formula:

SUMMARY OF THE INVENTION

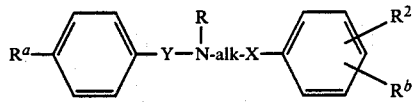

and their salts,
wherein
$R^a$ is —$NO_2$, —$NH_2$ or —$NHSO_2R^1$ where $R^1$ is a $C_1$–$C_4$ alkyl group;
$R^b$ is —$NO_2$, —$NH_2$ or $R^3$ where $R^3$ is —$NHSO_2$(-$C_1$–$C_4$ alkyl) or —$CONR^4R^5$ where $R^4$ and $R^5$ are each independently H or $C_1$–$C_4$ alkyl or together with the nitrogen atom to which they are attached represent a 1-pyrrolidinyl, piperidino, morpholino or N-methylpiperazin-1-yl group; with the proviso that when one of $R^a$ and $R^b$ is —$NO_2$, then the other is not —$NH_2$;
X is O, S or a direct link;
Y is an ethylene group optionally substituted by a methyl group;
"alk" is an ethylene, trimethylene or tetramethylene group, "alk" being optionally substituted by a methyl group;
R is $C_1$–$C_4$ alkyl; and
$R^2$ is H, halo, $CF_3$ or $C_1$–$C_4$ alkyl.

Formula (A) includes compounds which are antiarrhythmic agents, and compounds which are synthetic intermediates useful in the preparation of these antiarrhythmic agents. Those compounds having antiarrhythmic activity have the formula (I) set out below: the remaining compounds are synthetic intermediates only.

The invention thus provides antiarrhythmic agents of the formula:

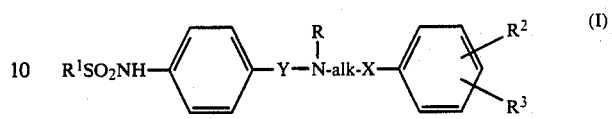

and their pharmaceutically acceptable salts,
wherein
R and $R^1$ are each independently $C_1$–$C_4$ alkyl;
X is O, S or a direct link;
Y is an ethylene group optionally substituted by a methyl group;
"alk" is an ethylene, trimethylene or tetramethylene group, "alk" being optionally substituted by a methyl group;
$R^2$ is H, halo, $CF_3$ or $C_1$–$C_4$ alkyl; and
$R^3$ is a group of the formula —$NHSO_2$($C_1$–$C_4$ alkyl) or —$CONR^4R^5$ wherein $R^4$ and $R^5$ are each independently H or $C_1$–$C_4$ alkyl or together with the nitrogen atom to which they are attached represent a 1-pyrrolidinyl, piperidino, morpholino or N-methylpiperazin-1-yl group.

"Halo" means F, Cl, Br or I. $C_3$ and $C_4$ alkyl groups can be straight or branched chain.

R is preferably $CH_3$ or $C_2H_5$, most preferably $CH_3$. $R^1$ is preferably $CH_3$. Examples of "alk" are —($CH_2$)$_n$— where n is 2, 3 or 4, —$CH(CH_3)CH_2$—, —$CH_2CH(CH_3)$—, —$CH(CH_3)CH_2CH_2$— and —$CH_2CH_2CH(CH_3)$—. "Alk" is preferably —($CH_2$)$_n$— where n is 2, 3 or 4, —$CH(CH_3)CH_2$— or —$CH_2CH(CH_3)$—. "Alk" is most preferably —($CH_2$)$_2$—. X is preferably O. Y is preferably —($CH_2$)$_2$—. $R^2$ is preferably H, $CH_3$ or Cl. $R^2$ is most preferably H. $R^3$ is preferably —$CONH_2$, —$CONHCH_3$, —$CON(C_2H_5)_2$;

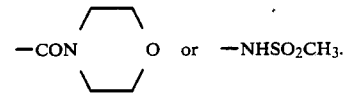

$R^3$ is most preferably —$NHSO_2CH_3$.

One preferred group of compounds has the formula (I) as defined above wherein R, $R^1$, $R^2$ $R^3$ and "alk" are as defined for formula (I), Y is —($CH_2$)$_2$—, and X is O or S. Another preferred group has the formula (I) wherein R, $R^1$, $R^2$, $R^3$ and "alk" are as defined for formula (I), X is a direct link, and Y is —($CH_2$)$_2$—.

The preferred individual compounds have the formulae:

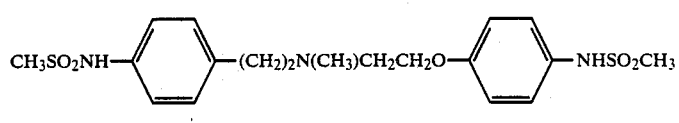

and

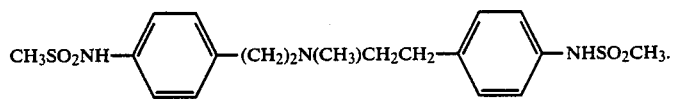

The first method compound is the most preferred.

Thus the present invention provides a pharmaceutical composition comprising a compound of the formula (I) as defined above or pharmaceutically acceptable salt thereof, together with a pharmaceutically acceptable diluent or carrier.

The invention also provides a method of preventing or reducing cardiac arrhythmias in a human being, which comprises administering to said human an effective amount of a compound of the formula (I) or pharmaceutically acceptable salt thereof, or of a pharmaceutical composition as defined above.

The invention yet further provides a compound of the formula (I) or a pharmaceutically acceptable salt thereof, for use as a medicament, particularly as an antiarrhythmic agent.

The invention also provides the use of a compound of the formula (I), or of a pharmaceutically acceptable salt thereof, for the manufacture of a medicament for the prevention or reduction of cardiac arrhythmias.

DETAILED DESCRIPTION OF THE INVENTION

Route I

The compounds of the formula (I) can be prepared by the following general route, in which R, $R^1$, $R^2$, $R^3$, alk, X and Y are as defined for formula (I). It starts from a compound in which $R^a$ is —$NH_2$:

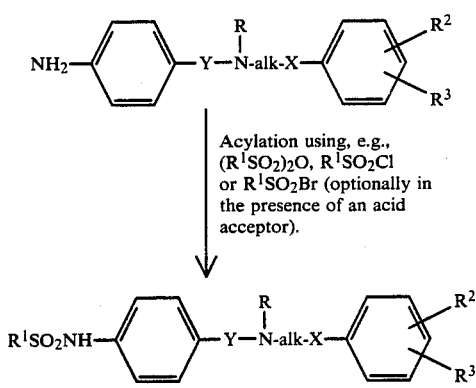

The reaction is typically carried out in a suitable organic solvent at room temperature, and optionally in the presence of a base ("acid acceptor") such as pyridine, triethylamine, sodium bicarbonate or potassium carbonate. The presence of an acid acceptor is especially useful when an alkanesulphonyl chloride or bromide is used as the acylating agent. It is preferred to use the sulphonic anhydride $(R^1SO_2)_2O$ in methylene chloride or sulphonyl chloride $R^1SO_2Cl$ in pyridine as the sulphonylating agent. The product (I) can then be isolated and purified by conventional techniques.

Route II

When $R^3$ is —$NHSO_2(C_1-C_4$ alkyl), then the following route, starting from an intermediate in which $R^a$ and $R^b$ are —$NH_2$, is particularly useful:

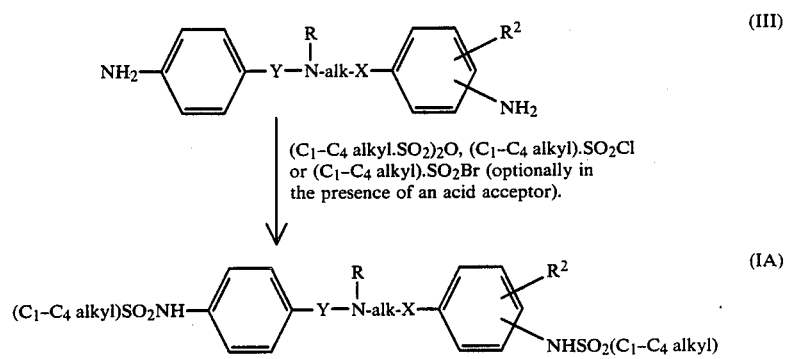

R, $R^2$, X, Y and "alk" are as defined for formula (I).

The reaction can be carried out similarly to Route I, although at least 2 equivalents of the sulphonylating agent must of course be used and, in the end producer (IA), each alkylsulphonamido group will be the same.

Route III

When $R^3$ is —$NHSO_2(C_1-C_4$ alkyl), then the following route, starting from a compound in which $R^b$ is —$NH_2$, can also be used:

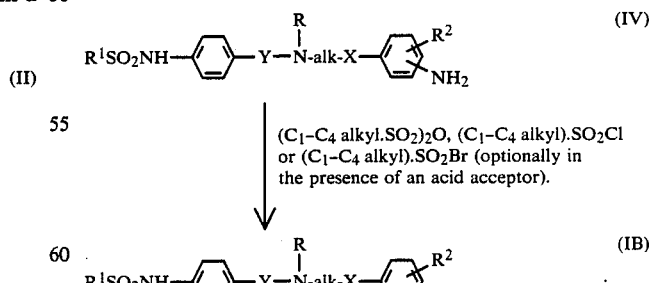

R, $R^1$, $R^2$, X, Y and "alk" are as defined for formula (I). The reaction can again be carried out similarly to Route I. Clearly this route can be used to prepare end products in which the alkanesulphonamido substituents are different.

The novel intermediates used in Routes I to III also form a part of the invention and these have the formula (A) as previously defined with the additional proviso that either at least one of $R^a$ and $R^b$ is nitro, or at least one of $R^a$ and $R^b$ is amino.

The starting materials for the above routes are obtainable by conventional methods, e.g. as follows:

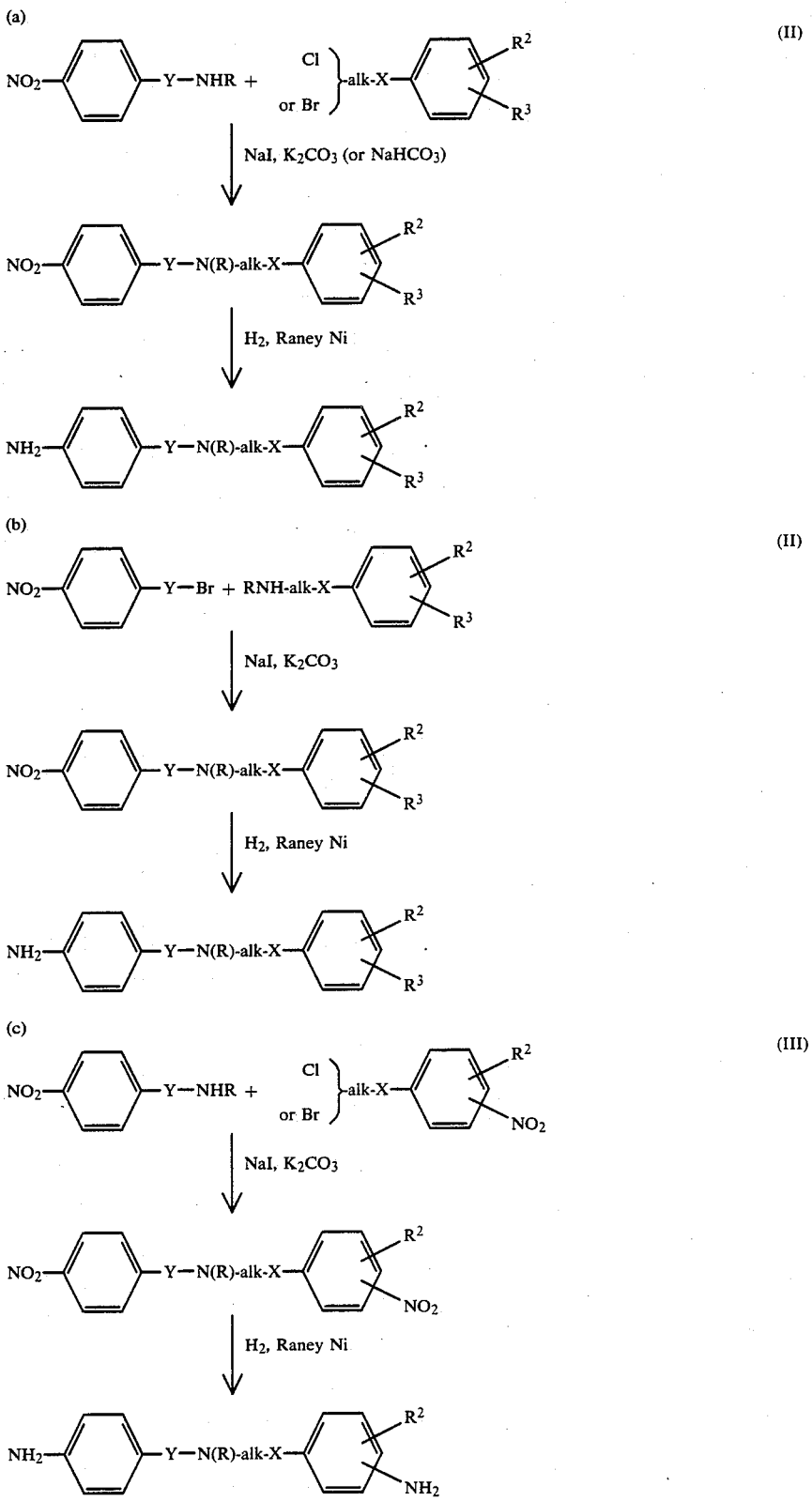

(d) For intermediates in which X is O or S only:

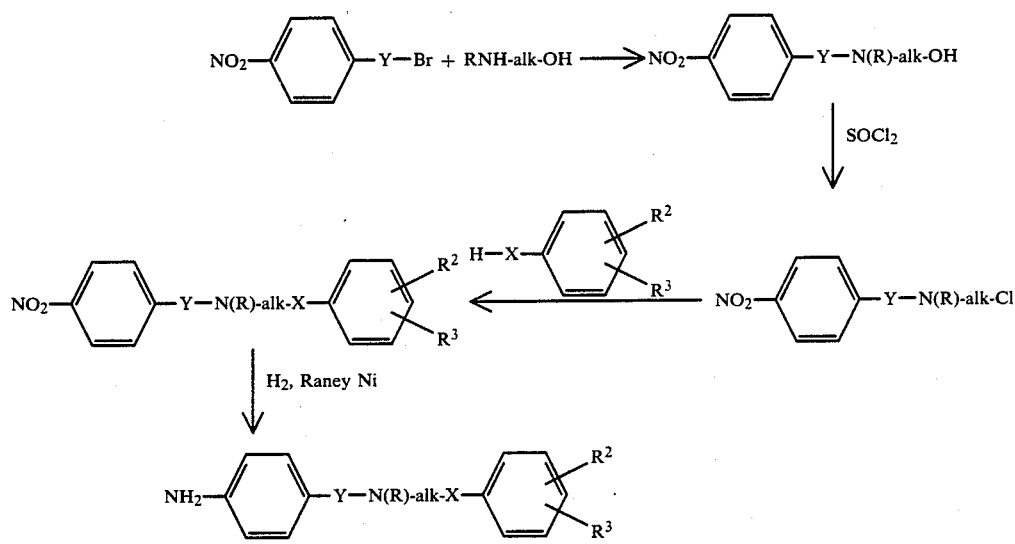

(IIA)

[X = O or S only.]

In a modification of this route, a thiophenol or phenol in which R³ is nitro can be used. The hydrogenation step will also reduce this nitro group to amino, thus producing an intermediate of the formula (III) in which X is S or O.

A further modification of this route, useful in preparing certain compounds of the formula (IIA) having "alk" as —CH(CH₃)CH₂— or —CH₂CH(CH₃)—, is as follows:

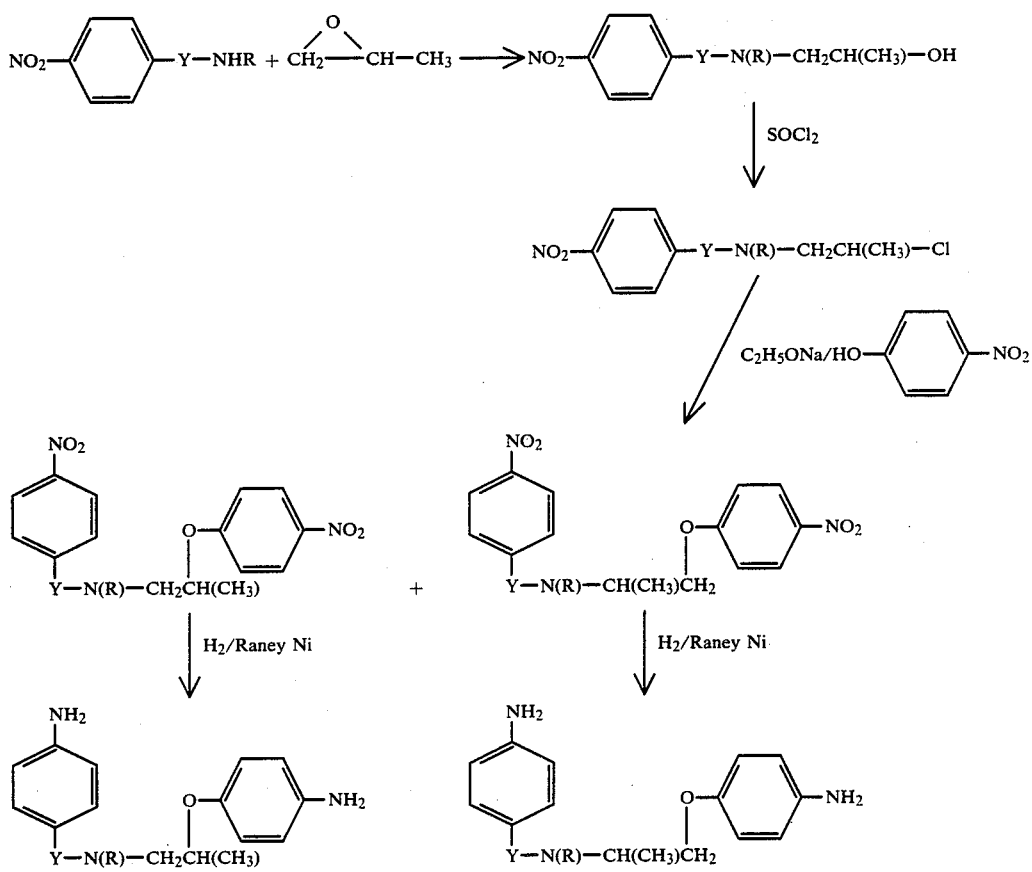

The mixture of the 2 nitro-containing compounds is believed to result from the competitive ring opening of an intermediate aziridinium cation formed in the reaction. The nitro-containing intermediates can be separated by chromatography prior to the catalytic hydrogenation step.
Where the starting materials used in (a) to (g) above are not known compounds, they can again be prepared by conventional techniques e.g. as follows:
(e)
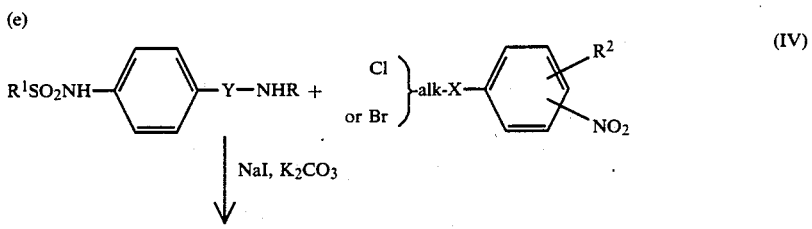
(IV)
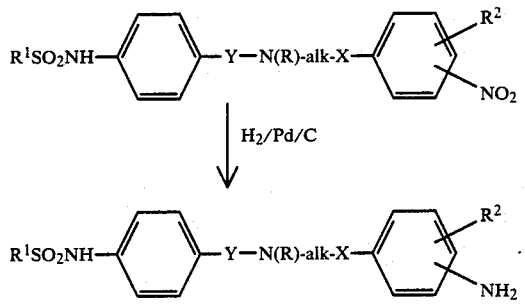
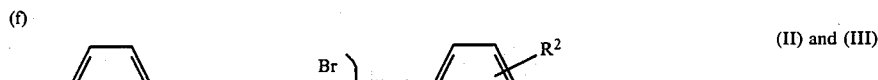
(f)
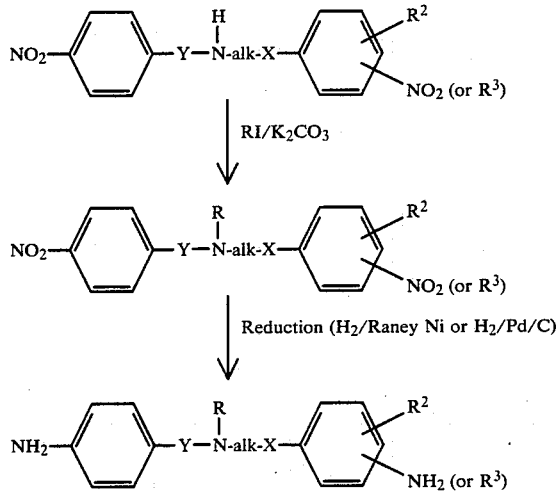
(II) and (III)
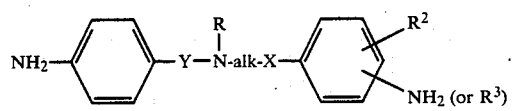
and (g)
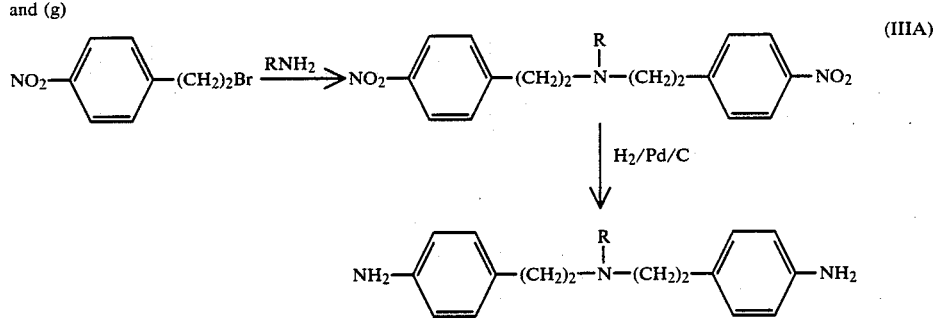
(IIIA)

(i) 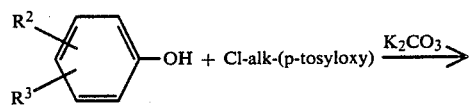

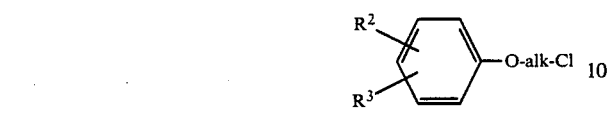

(ii) 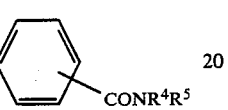

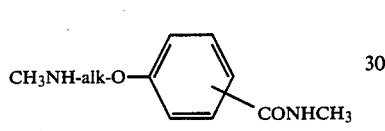

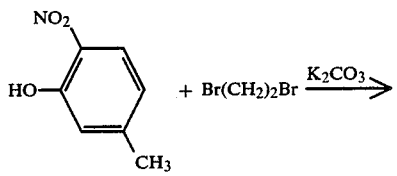

(iv) 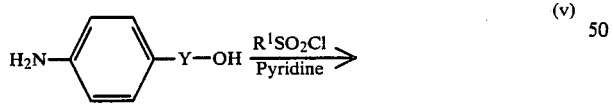

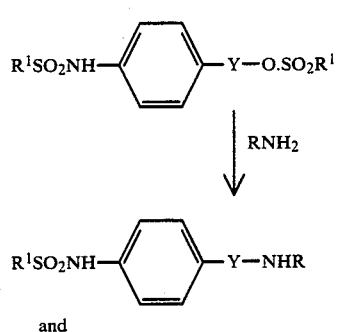

-continued (vi) 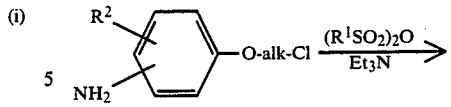

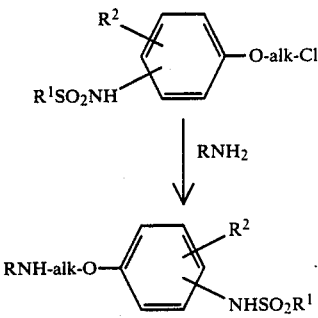

Route IV

The compounds of the formula (I) can also be prepared as follows:

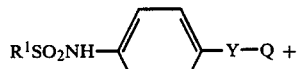

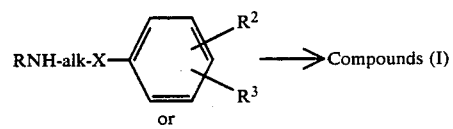

or

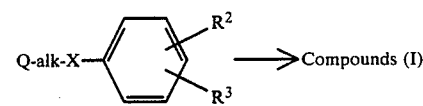

In the above, R, $R^1$, $R^2$, $R^3$, X, Y and alk are as defined for formula (I), and Q is a leaving group, e.g. chloro, bromo, iodo, $C_1$–$C_4$ alkanesulphonyloxy (particularly methanesulphonyloxy), benzenesulphonyloxy or toluenesulphonyloxy. The presence of an acid acceptor such as sodium bicarbonate, triethylamine or potassium carbonate is optional, but is preferred when Q is halo.

The reaction is typically carried out in an organic solvent, e.g. ethanol, at up to the reflux temperature, typically at up to about 120° C. It is preferred to carry out the reaction under reflux. The product can then be isolated and purified by conventional means.

The starting materials can again be obtained conventionally.

When the compounds of the formula (1) contain one or more optically active centres, then the invention encompasses both resolved and unresolved forms.

The pharmaceutically acceptable salts of the compounds of the formula (I) include acid addition salts formed from acids which form non-toxic acid addition salts containing pharmaceutically acceptable anions, such as hydrochloride, hydrobromide, hydroiodide, sulphate or bisulphate, phosphate or hydrogen phosphate, acetate, maleate, fumarate, lactate, tartrate, citrate, gluconate, benzoate, methanesulphonate, besylate and p-toluenesulphonate salts. The compounds also form metal salts, preferred examples of which are the alkaline earth and alkali metal salts. The sodium and potassium salts are most preferred. The salts are preparable by conventional techniques.

For assessment of effects of the compounds on atrial refractoriness, guinea pig right hemiatria are mounted in a bath containing physiological salt solution, and one end is connected to a force transducer. Tissues are stimulated at 1 Hz using field electrodes. Effective refractory period (ERP) is measured by introducing premature stimuli ($S_2$) after every 8th basic stimulus ($S_1$). The $S_1S_2$ coupling interval is gradually increased until $S_2$ reproducibly elicits a propagated response. This is defined as the ERP. The concentration of compound required to increase ERP by 25% ($ED_{25}$) is then determined. ERP is also measured in guinea pig right papillary muscles incubated in physiological salt solution. Muscles are stimulated at one end using bipolar electrodes and the propagated electrogram is recorded at the opposite end via a unipolar surface electrode. ERP is determined as above using the extrastimulus technique. Conduction time is obtained from a digital storage oscilloscope by measuring the interval between the stimulus artifact and the peak of the electrogram (i.e. the time required for the impulse to travel along the length of the muscle).

Atrial and ventricular ERP's are also measured in anaesthetised or conscious dogs by the extrastimulus technique whilst the atrium or right ventricle is being paced at a constant rate.

The compounds of the formula (I) can be administered alone but will generally be administered in admixture with a pharmaceutical carrier selected with regard to the intended route of administration and standard pharmaceutical practice They can be administered both to patients suffering from arrhythmias and also prophylactically to those likely to develop arrhythmia. For example they may be administered orally in the form of tablets containing such excipients as starch of lactose, or in capsules either alone or in admixture with excipients, or in the form of elixirs or suspensions containing flavouring or colouring agents. They may be injected parenterally, for example, intravenously, intramuscularly or subcutaneously. For parenteral administration, they are best used in the form of a sterile aqueous solution which may contain other solutes, for example, enough salts or glucose to make the solution isotonic.

For administration to man in the curative or prophylactic treatment of cardiac conditions such as ventricular and supraventricular arrhythmias, including atrial and ventricular fibrillation, it is expected that oral dosages of the compounds of the formula (I) will be in the range from 1 to 75 mg daily, taken in up to 4 divided doses per day, for an average adult patient (70 kg). Dosages for intravenous administration would be expected to be within the range 0.5 to 10 mg per single dose as required. A severe cardiac arrhythmia is preferably treated by the i.v. route in order to effect a rapid conversion to the normal rhythm. Thus for a typical adult patient individual tablets or capsules might for example contain 1 to 25 mg of active compound, in a suitable pharmaceutically acceptable vehicle or carrier. Variations may occur depending on the weight and condition of the subject being treated as will be known to medical practitioners.

The following Examples, in which all temperatures are in °C., illustrate the preparation of the compounds of the formula (I). In these Examples, 3 atmospheres is equivalent to $3.04 \times 10^5$ Pa, and 50 p.s.i. to $3.45 \times 10^5$ Pa.

EXAMPLE 1

(A)

4-{2-[N-Methyl-N-(4-nitrophenethyl)aminoethoxy]}benzamide

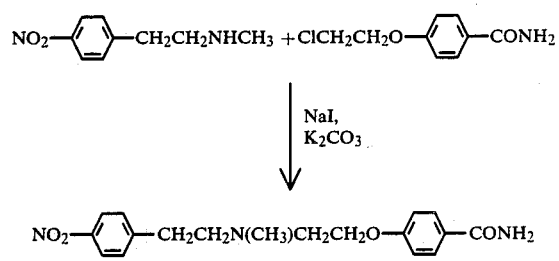

To a solution of N-methyl-4-nitrophenethylamine (1.8 g) [JO C., (1956), 21, 45]and 4-(2-chloroethoxy)benzamide (see Preparation 12) in acetonitrile (100 ml) was added potassium carbonate (3.0 g) and sodium iodide (1.5 g) and the suspension stirred at reflux for 72 hours. After evaporation, a 2N aqueous sodium bicarbonate solution was added to the residual oily solid and then extracted three times with methylene chloride. The combined organic layers were washed with a saturated aqueous brine solution, dried over magnesium sulphate, filtered and evaporated to give a yellow oil. Trituration of the oil with diisopropyl ether gave 2.3 g of a yellow solid which was crystallised from toluene to give the title compound (1.4 g), m.p. 116°-118°, which was used directly without further purification.

(B)

4-{2-[N-(4-Aminophenethyl)-N-methylamino]ethoxy]}benzamide

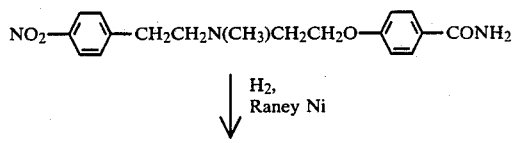

A solution of 4-{2-[N-methyl-N-(4-nitrophenethyl)amino]ethoxy}benzamide (1.4 g) in ethanol (100 ml) was stirred for 16 hours at room temperature under three atmospheres of hydrogen in the presence of Raney nickel ("Nicat 102", Trade Mark). The reaction mixture was filtered and evaporated to dryness to give a yellow solid (1.2 g) which crystallised from ethyl acetate to give the title compound, (1.1 g), m.p. 110°-112°.

Analysis % Found: C,69.1; H,7.3;N,13.05; Calculated for $C_{18}H_{23}N_3O_2$: C,69.0;H,7.4;N,13.4

(C) 4-{2-[N-Methyl-N-(4-methanesulphonamidophenethyl)amino]ethoxy}benzamide

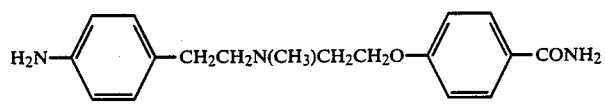

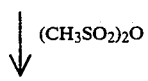

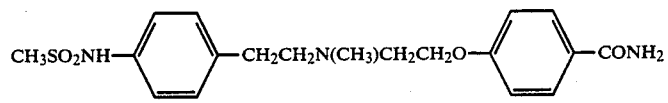

in part (C), followed by treatment with ethereal hydrogen chloride, filtering off the resulting hydrochloride salt, and recrystallising it from ethyl acetate/methanol.

---

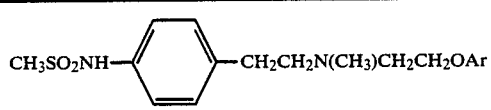

| Example No. | Ar | Form Isolated | Recrystallization Solvent | m.p. (°C.) | Analysis % (Theoretical in Brackets) | | |
|---|---|---|---|---|---|---|---|
| | | | | | C | H | N |
| 2 | —⌬—CON(Et)₂ | Free base | Diisopropyl ether/ ethyl acetate | 97–98 | 61.7 (61.7 | 7.25 7.4 | 9.1 9.4) |
| 3 | —⌬—CON⟨morpholine⟩ | Hydrochloride hemihydrate | Ethyl acetate/ methanol | 198–201 | 55.0 (54.5 | 6.3 6.6 | 8.0 8.3) |
| 4 | —⌬(CONH₂) | Free base | Ethyl acetate | 104–106 | 57.8 (58.3 | 6.4 6.4 | 10.6 10.7) |
| 5 | —⌬(CONH₂)(CH₃) | Hydrochloride | Ethyl acetate/ methanol | 124–126 | 54.7 (54.3 | 6.7 6.4 | 9.1 9.5) |

---

A solution of 4-{2-[N-(4-aminophenethyl)-N-methylamino]ethoxy}benzamide (1.0 g) and methanesulphonic anhydride in dry methylene chloride (50 ml) was stirred at room temperature for 16 hours. After evaporation a 2N aqueous sodium bicarbonate solution was added to the residue followed by extraction three times with methylene chloride. The combined organic layers were dried over magnesium sulphate, filtered and evaporated to give a light brown solid. Crystallisation from toluene/ethyl acetate gave the title compound (0.31 g), m.p. 147°.

Analysis %: Found: C,58.35; H,6.7; N,10.45; Calculated for C₁₉H₂₅N₃O₄S: C,58.3; H,6.4; N,10.7.

EXAMPLES 2 TO 5

The following compounds were prepared similarly to Example 1 parts (A) to (C) from appropriate starting materials. In Examples 3 and 5, the products were characterised as hydrochloride salts by adding ethyl acetate to the solid resulting from the second evaporation step

EXAMPLE 6

(A) N-Methyl-4-(2-methylaminoethoxy)benzamide

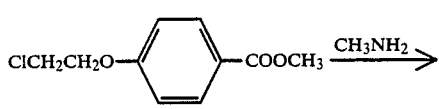

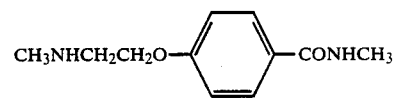

To a 33% solution of methylamine in industrial methylated spirits (50 ml) was added methyl 4-(2-chloroethoxy)benzoate (4.3 g) (see Preparation 11) and the mixture was stirred while heating at 100° in a 130 ml sealed pressure vessel for 16 hours. After evaporation to dryness, the resultant solid was added to 10 ml of 2N aqueous sodium hydroxide solution and extracted three times with methylene chloride. The combined organic layers were dried over anhydrous magnesium sulphate, filtered and evaporated to give a colourless solid. Crystallisation from isopropanol gave the title compound, (2.1 g), m.p. 95°–96°.

Analysis %: Found: C,63.7; H,7.6; N,13.4; Calculated for $C_{11}H_{16}N_2O_2$: C,63.4; H,7.7; N,13.45.

(B)
N-Methyl-4-{2-[N'-methyl-N'-(4-nitrophenethyl)amino]ethoxy}benzamide

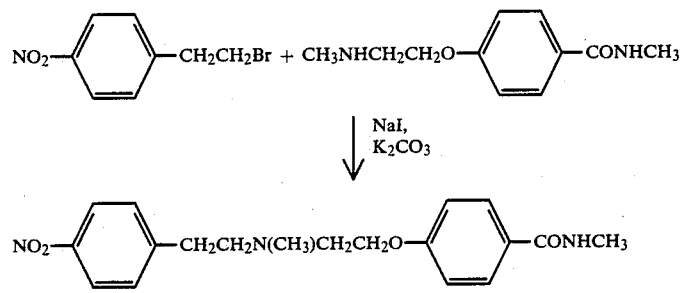

To a solution of N-methyl-4-(2-methylaminoethoxy)-benzamide and 4-nitrophenethyl bromide in acetonitrile (100 ml) was added potassium carbonate (3.0 g) and sodium iodide (1.5 g) and the suspension was stirred at reflux for 72 hours. After evaporation, a 2N aqueous sodium hydroxide solution was added followed by extraction three times with methylene chloride. The combined organic layers were washed with a saturated aqueous brine solution, dried over magnesium sulphate, filtered and evaporated to give a yellow oil. Trituration of the oil with diisopropyl ether gave the title compound as a yellow solid, (2.4 g), which was used without further purification.

N.m.r. (CDCl$_3$): ppm, δ=7.9 (d, 2H); 7.52 (d, 2H); 7.12 (d, 2H); 6.63 (d, 2H); 3.9 (t, 2H); 2.8 (m, 9H); 28 (s, 3H).

(C)
N-Methyl-4-{2-[N'-(4-aminophenethyl)-N'-methylamino]ethoxy}benzamide

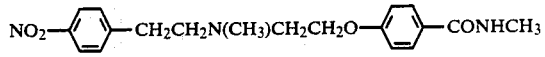

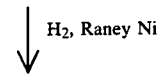

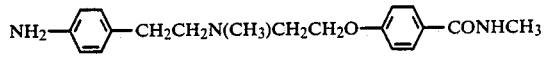

A solution of N-methyl-4-{2-[N'-methyl-N'-(4-nitrophenethyl)amino]ethoxy}benzamide (2.3 g) in ethanol (100 ml) was stirred for 16 hours at room temperature under three atmospheres of hydrogen in the presence of Raney nickel ("Nicat 102"-Trade Mark). The reaction mixture was filtered and evaporated to dryness to give a yellow oil (2.1 g). Chromatography on silica ("Kieselgel 60"-Trade Mark) eluting with ethyl acetate gave the title compound as a colourless oil, (1.7 g), which was used directly without further purification.

N.m.r. (CDCl$_3$): ppm, δ=7.72 (d, 2H); 7.0 (d, 2H); 6.92 (d, 2H); 6.62 (d, 2H); 3.0 (d, 3H); 2.88 (t, 2H); 2.7 (s, 4H); 2.42 (s, 3H).

(D)
N-Methyl-4-{2-[N'-(4-methanesulphonamidophenethyl)-N'-methylamino]ethoxy}benzamide hydrochloride

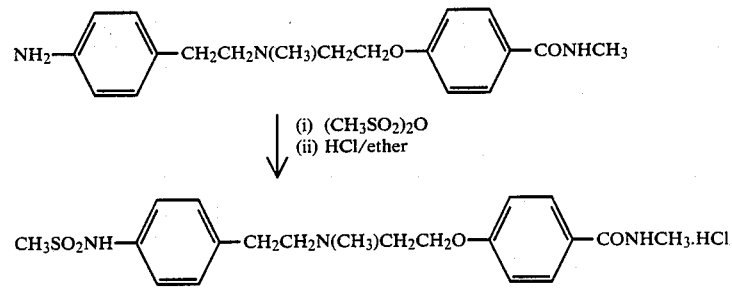

A solution of N-methyl-4-{-2-[N'-(4-aminophenethyl)-N'-methylamino]ethoxy}benzamide (1.6 g) and methanesulphonic anhydride (0.87 g) in dry methylene chloride (50 ml) was stirred at room temperature overnight. After evaporation, the resultant oily solid was treated with a 2N aqueous sodium bicarbonate solution and extracted three times with methylene chloride. The combined organic layers were washed with a saturated aqueous brine solution, dried over magnesium sulphate, filtered and evaporated. Chromatography on silica ["Kieselgel 60"-Trade Mark] eluting with ethyl acetate gave a colourless oil (0.52 g). The oil was dissolved in ethyl acetate and an ethereal solution of hydrogen chloride was added until precipitation was complete. The colourless solid was filtered off and crystallised from ethyl acetate/methanol to give the title compound, (0.2 g), m.p. 160°.

Analysis %: Found: C,54.2; H,6.6; N,9.25; Calculated for $C_{20}H_{27}N_3O_4S.HCl$: C,54.35; H,6.4; N,9.5.

EXAMPLE 7

(A)

1-(4-Nitrophenoxy)-2-[N-methyl-N-(4-nitrophenethyl)amino]ethane

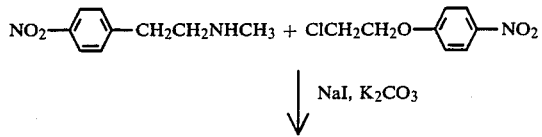

↓ NaI, K₂CO₃

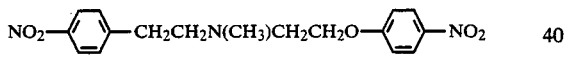

To a solution of N-methyl-4-nitrophenethylamine (1.5 g) (J.O.C., [1956], 21, 45) and 2-[4-nitrophenoxy]ethyl chloride (1.55 g) (C.A., [1955], 49, 3163e) in acetonitrile (50 ml) was added potassium carbonate (1.25 g) and sodium iodide (1.2 g) and the suspension was stirred at reflux for 72 hours. After evaporation to dryness, the residual oily solid was partitioned between a 2N aqueous sodium bicarbonate solution and ethyl acetate. After two further extractions with ethyl acetate, the organic portions were combined, washed with a saturated aqueous brine solution, dried over magnesium sulphate, filtered and evaporated. The resultant orange solid (2.7 g) was crystallised from ethanol to give the title compound, (1.9 g), m.p. 74°.

Analysis %: Found: C,58.75; H,5.4; N,12.15; Calculated for $C_{17}H_{19}N_3O_4$: C,59.1; H,5.5; N,12.2.

(B)

1-(4-Aminophenoxy)-2-[N-(4-aminophenethyl)-N-methylamino]ethane

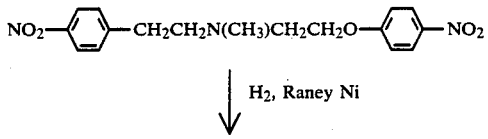

↓ H₂, Raney Ni

-continued

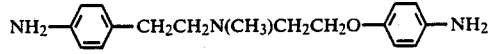

A solution of 1-(4-nitrophenoxy)-2-[N-methyl-N-(4-nitrophenethyl)amino]ethane (1.5 g) in ethanol (100 ml) was stirred for hours at room temperature under three atmospheres of hydrogen in the presence of Raney nickel ("Nicat 102"-Trade Mark). The reaction mixture was filtered and evaporated to dryness. The residual oil was re-dissolved in ether, filtered and evaporated to give a yellow solid (1.1 g), which was crystallised from ethyl acetate/60°-80° petroleum ether to give the title compound, (0.9 g), m.p. 73°-74°.

Analysis %: Found: C,71.3; H,8.1; N,14.7; Calculated for $C_{17}H_{23}N_3O$: C,71.55; H,8.1; N,14.7.

(C)

1-(4-Methanesulphonamidophenoxy)-2-[N-(4-methanesulohonamidophenethyl)-N-methylamino]ethane

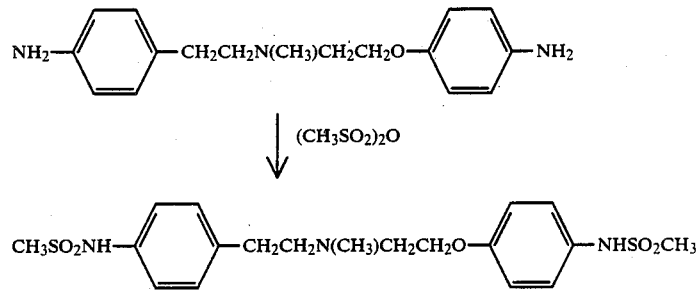

A solution of 1-(4-aminophenoxy)-2-[N-(4-aminophenethyl)-N-methylamino]ethane (0.75 g) and methanesulphonic anhydride (1.0 g) in dry methylene chloride (50 ml) was stirred at room temperature overnight. After evaporation, the resultant oil was partitioned between a 2N aqueous sodium bicarbonate solution and ethyl acetate. After two further extractions with ethyl acetate, the organic portions were combined, dried over magnesium sulphate, filtered and evaporated. The resultant colourless solid (1.2 g) was crystallised from ethyl acetate/methanol to give the title compound, (0.6 g), m.p. 147°-149°.

Analysis %: Found: C,52.1; H,6.25; N,9.45; Calculated for $C_{19}H_{27}N_3O_5S_2$: C,51.9; H,6.15; N,9.4.

EXAMPLES 8 to 14

The following compounds were prepared similarly to the procedure of the previous Example parts (A) to (C), starting from corresponding starting materials except that in part (A) 2-(nitrophenoxy)ethyl bromides rather than chlorides were used, and were isolated in the forms indicated. The hydrochloride salts were prepared by dissolving the residue from the last evaporation step in ethyl acetate, adding ethereal hydrogen chloride, filtering off the resultant precipitate of the hydrochloride salt, followed by recrystallisation from the stated solvent.

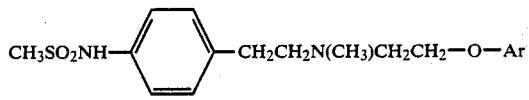

| Example No. | Ar | Form Isolated | Recrystallization Solvent | m.p. (°C.) | Analysis % (Theoretical in Brackets) | | |
|---|---|---|---|---|---|---|---|
| | | | | | C | H | N |
| 8 | NHSO₂CH₃ (para) | Free base | 60–80° Petroleum ether/ethyl acetate | 113-4 | 51.9 (51.7 | 6.45 6.2 | 9.0 9.5) |
| 9 | NHSO₂CH₃ (ortho) | Hydrochloride | Ethyl acetate/ methanol | 178-80 | 47.7 (47.7 | 6.0 5.9 | 8.6 8.8) |
| 10 | NHSO₂CH₃, CH₃ | Hydrochloride hydrate | Ethyl acetate/ methanol | 185 (foams) | 47.0 (47.1 | 6.1 6.3 | 8.0 8.2) |

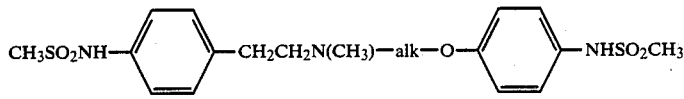

| Example No. | "Alk" | Form Isolated | Recrystallization Solvent | m.p. (°C.) | Analysis % 78 (Theoretical in Brackets) | | |
|---|---|---|---|---|---|---|---|
| | | | | | C | H | N |
| 11 | —(CH₂)₃— | Hydrochloride | EtOAc/MeOH | 125°* | 48.8 48.5 | 6.2 6.4 | 8.5) 8.2 |
| 12 | —(CH₂)₄— | Hydrochloride Hemihydrate | EtOAc/MeOH | >90°* | (49.0 49.2 | 6.5 6.6 | 8.2) 7.7 |

*Foams

The starting materials 4-(3-bromopropoxy)nitrobenzene and 4-(4-bromobutoxy)nitrobenzene are described, respectively, in J.A.C.S. (1951), 73, 3159 and C.A., 59, 9883.

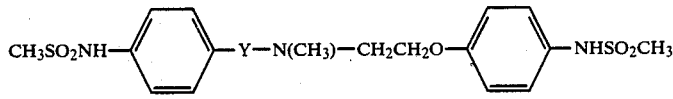

| Example No. | Y | Form Isolated | Recrystallization Solvent | m.p. (°C.) | Analysis % (Theoretical in Brackets) | | |
|---|---|---|---|---|---|---|---|
| | | | | | C | H | N |
| 13 | —CH₂CH— \| CH₃ | Hydrochloride Hemihydrate | EtOAc/MeOH | >106° (hygroscopic) | 47.8 (47.9 | 6.4 6.2 | 8.2 8.4) |
| 14 | —CHCH₂— \| CH₃ | Hydrochloride | EtOAc/MeOH | >98° (hygroscopic) | 49.0 (48.8 | 6.2 6.15 | 8.2 8.5) |

The starting materials N-methyl-1-(4-nitrophenyl)-2-propylamine and N-methyl-2-(4-nitrophenyl)-1-propylamine are described in J.A.C.S., (1946), 68, 1153.

EXAMPLES 15 and 16

The following compounds were prepared similarly to the procedure of Example 7 parts (B) and (C) using corresponding starting materials [see Preparation 6 parts (C) and (D)] except that in part (C) methanesulphonyl chloride in pyridine was used rather than methanesulphonic anhydride in methylene chloride. In Example 16, the hydrochloride salt was obtained as described in the relevant description relating to Examples 8 to 14.

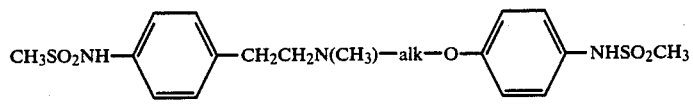

| Example No. | Alk | Form Isolated | Recrystallization Solvent | m.p. (°C.) | Analysis % (Theoretical in Brackets) | | |
|---|---|---|---|---|---|---|---|
| | | | | | C | H | N |
| 15 | CH$_3$<br>|<br>—CH—CH$_2$— | Free base | Hexane/EtOAc | 120° | 52.8<br>(52.7 | 6.5<br>6.4 | 8.9<br>9.2) |
| 16 | CH$_3$<br>|<br>—CH$_2$—CH— | Hydrochloride<br>Hemihydrate | EtOAc/MeOH | >100°<br>(hygroscopic) | 48.1<br>(47.9 | 6.3<br>6.2 | 8.2<br>8.4) |

EXAMPLE 17

(A) 2-[N-Methyl-N-(4-nitrophenethyl)amino]ethanol

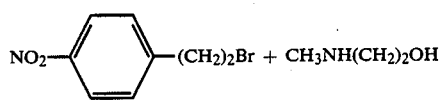

↓

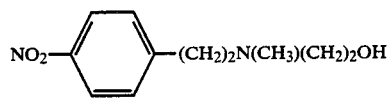

A mixture of 4-nitrophenethyl bromide (11.5 g) and N-methylethanolamine (8.25 g) in xylene (100 ml) was stirred at reflux for 16 hours. After evaporation, the residue was partitioned between 5% aqueous sodium bicarbonate and methylene chloride. The organic liquors were washed with saturated aqueous brine, dried (MgSO$_4$), filtered and evaporated to give an orange oil (10.1 g). Chromatography on silica ("Kieselgel 60"-Trade Mark) eluting with ethyl acetate followed by collection and evaporation of suitable fractions gave the title compound as a yellow oil, (7.5 g).

N.m.r. (CDCl$_3$): ppm, δ=8.05 (d, 2H); 7.2 (d, 2H); 3.52 (t, 2H); 2.61 (m, 6H); 2.3 (s, 3H).

(B) 2-[N-Methyl-N-(4-nitrophenethyl)amino]ethyl chloride hydrochloride

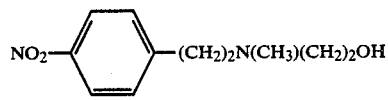

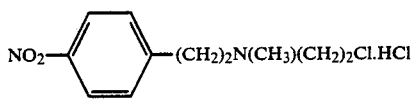

To a solution of 2-[N-methyl-N-(4-nitrophenethyl)amino]ethanol (8.0 g) in dry methylene chloride (75 ml) was added dropwise thionyl chloride (3 ml) with stirring at 0° C. The mixture was allowed to warm to ambient temperature and stirred for 16 hours. The resultant solid was filtered, washed with dry ether and dried to give a colourless product (7.1 g). Crystallisation from ethyl acetate/methanol gave the title compound, 6.0 g, m.p. 168°–169°.

Analysis %: Found: C,46.8; H,5.8; N,9.85; Calculated for C$_{11}$H$_{15}$ClN$_2$O$_2$.HCl: C,47.3; H,5.8; N,10.0.

(C)
2-[N-Methyl-N-(4-nitrophenethyl)amino]-1-(4-nitrophenylthio)ethane

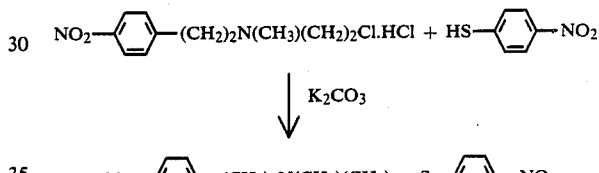

2-[N-Methyl-N-(4-nitrophenethyl)amino]ethyl chloride hydrochloride (3.0 g), 4-nitrothiophenol (1.7 g) and potassium carbonate (4.0 g) in acetonitrile (100 ml) were stirred at reflux for 16 hours. After evaporation, the residue was partitioned between water and ethyl acetate. The organic liquors were washed with saturated aqueous brine, dried (MgSO$_4$), filtered and evaporated to give an orange oil (3.6 g). Chromatography on silica ("Kieselgel 60"-Trade Mark) eluting with ethyl acetate followed by collection of suitable fractions gave on evaporation the title compound as a yellow solid, (3.05 g), m.p. 56°–7°.

Analysis %: Found: C,56.8; H,5.3; N,11.7; Calculated for C$_{17}$H$_{19}$N$_3$O$_4$S: C,56.5; H,5.3; N,11.6.

(D)
1-(4-Aminophenylthio)-2-[N-(4-aminophenethyl)-N-methylamino]ethane

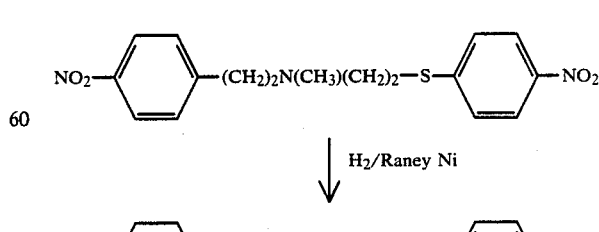

The title compound was prepared by the hydrogenation of 2-[N-methyl-N-(4-nitrophenethyl)amino]-1-(4-nitrophenylthio)ethane over Raney nickel according to the procedure of Example 7(B).

N.m.r. (CDCl$_3$): ppm, δ=7.25 (d, 2H); 6.98 (d, 2H); 6.60 (m, 4H); 2.92 (t, 2H); 2.60 (m, 6H); 2.32 (s, 3H).

The starting material 2-chloro-4-nitrophenol is described in C.A., 34, 5574 (1940).

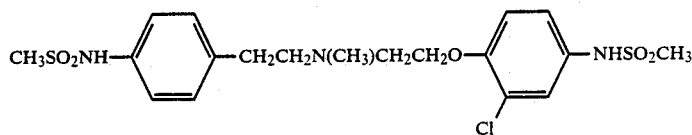

| Example No. | Form Isolated | Recrystallization Solvent | m.p. (°C.) | Analysis % (Theoretical in brackets) | | |
|---|---|---|---|---|---|---|
| | | | | C | H | N |
| 18 | Free base | Diethyl ether | 141–143 | 47.9 (47.8 | 5.5 5.6 | 8.8 8.5) |

EXAMPLE 19

(A)

1-(4-Methanesulphonamidophenoxy)-2-[N-methyl-N-(4-nitrophenethyl)amino]ethane

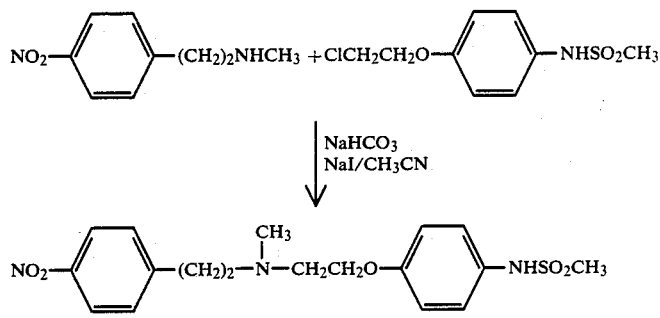

A suspension of N-methyl-4-nitrophenethylamine (1.1 g), 2-(4-methanesulphonamidophenoxy)ethyl chloride (1.5 g), sodium bicarbonate (0.5 g) and sodium iodide (0.9 g) in acetonitrile (100 ml) was stirred at reflux for 4 days. On evaporation to dryness the resultant oil was partitioned between 2N aqueous sodium bicarbonate solution and methylene chloride. After two further extractions with methylene chloride, the organic portions were combined, washed with saturated brine solution, dried over anhydrous magnesium sulphate, filtered and evaporated to dryness. The resultant brown oil was chromatographed on silica ("Kieselgel 60"-Trade Mark) eluting with ethyl acetate followed by collection and evaporation of suitable fractions to give the title compound as a yellow solid, (0.9 g).

N.m.r. (CDCl$_3$): δ=2.45 (s, 3H); 2.86 (m, 6H); 3.0 (s, 3H); 4.2 (t, 3H); 6.86 (d, 2H); 7.22 (d, 2H); 7.4 (d, 2H); 8.15 (d, 2H).

(E)

1-(4-Methanesulphonamidophenylthio)-2-[N-(4-methanesulphonamidophenethyl)-N-methylamino]ethane

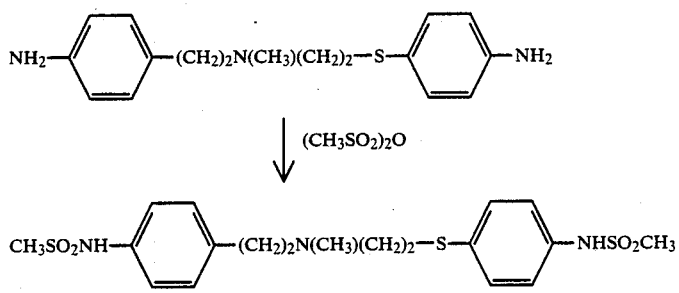

The title compound, m.p. 160°–163°, was prepared by the mesylation of the product of part (D) above using methanesulphonic anhydride according to the procedure of Example 7(C).

Analysis %: Found: C,49.5; H,6.1; N,8.6; Calculated for C$_{19}$H$_{27}$N$_3$O$_4$S$_3$: C,49.9; H,5.95; N,9.2.

EXAMPLE 18

The following compound was prepared similarly to the procedure of the previous Example parts (A) to (E), starting from corresponding starting materials, with the exception that the reductive step (D) was performed with SnCl$_2$ in hydrochloric acid, and that the mesylation step (E) was performed using methanesulphonyl chloride in pyridine.

(B)
1-(4-Methanesulphonamidophenoxy)-2-[N-methyl-N-(4-aminophenethyl)amino]ethane

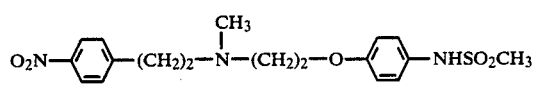

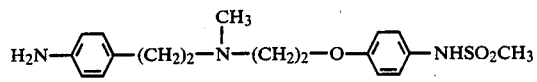

A solution of 1-(4-methanesulphonamidophenoxy)-2-[N-methyl-N-(4-nitrophenethyl)amino]ethane (0.9 g) in ethanol (100 ml) was stirred for 16 hours at room temperature under three atmospheres of hydrogen in the presence of Raney Nickel ("Nicat 102"-Trade Mark). The reaction mixture was filtered and evaporated to dryness. The resultant solid was crystallised from toluene to give the title compound as yellow crystals, (0.6 g), m.p. 155°–157°.

Analysis %: Found: C,59.9; H,7.1; N,11.2; Calculated for $C_{18}H_{25}N_3O_3S$: C,59.5; H,7.0; N,11.6.

(C)
1-(4-Methanesulphonamidophenoxy)-2-[N-4-methanesulphonamidophenethyl)-N-methylamino]ethane

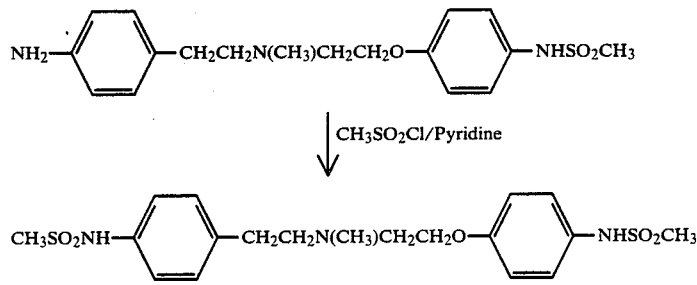

To a solution of 1-(4-methanesulphonamidophenoxy)-2-[N-methyl-N-(4-aminophenethyl)amino]ethane (0.15 g) in dry pyridine (3 ml) was added dropwise methanesulphonyl chloride (35.4 μl) and the mixture was stirred at room temperature overnight. After evaporation, the resultant oil was partitioned between 2N aqueous sodium bicarbonate solution and methylene chloride. After two further extractions with methylene chloride, the organic portions were combined. dried over anhydrous magnesium sulphate, filtered and evaporated. The resultant colourless solid (0.135 g) was crystallised from hexane/ethyl acetate to give the title compound (0.1 g), m.p. 151°–152°, confirmed spectroscopically to be identical to the product of Example 7(C).

Analysis %: Found: C,51.6; H,6.2; N,9.2; Calculated for $C_{19}H_{27}N_3O_5S_2$: C,51.9; H,6.15; N,9.4.

EXAMPLE 20

(A)
1-(4-Nitrophenoxy)-2-[N-methyl-N-(4-methanesulphonamidophenethyl)amino]ethane

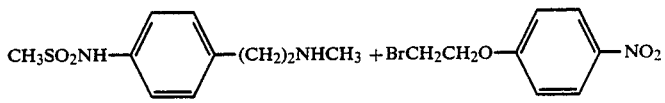

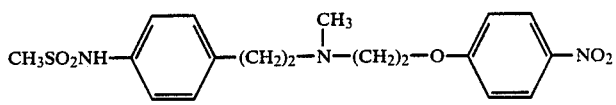

A solution of N-methyl-4-methanesulphonamidophenethylamine (1.0 g) (see Preparation 8), 2-(4-nitrophenoxy)ethyl bromide (1.2 g) (C.A., 54, 11046a), potassium carbonate (0.67 g) and sodium iodide (0.72 g) in acetonitrile (100 ml) was stirred at reflux for 3 days. On evaporation to dryness, the residual oil was partitioned between water and methylene chloride. After two further extractions with methylene chloride, the organic portions were combined, washed with saturated brine solution, dried over anhydrous magnesium sulphate, filtered and evaporated to dryness. The resultant yellow oil was taken up in hot methanol, cooled and the title compound crystallised as a colourless solid, (1.2 g).

N.m.r. (CDCl$_3$): δ=2.48 (s, 3H); 2.82 (m, 4H); 2.93 (t, 2H); 3.02 (s, 3H); 4.18 (t, 2H); 6.98 (d, 2H); 7.18 (d, 2H); 7.22 (d, 2H); 8.15 (d, 2H).

(B)
1-(4-Aminophenoxy)-2[N-methyl-N-(4-methanesulphonamidophenethyl)amino]ethane, dihydrochloride

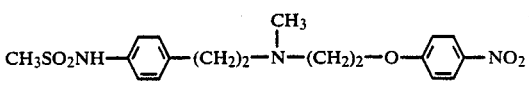

29
-continued

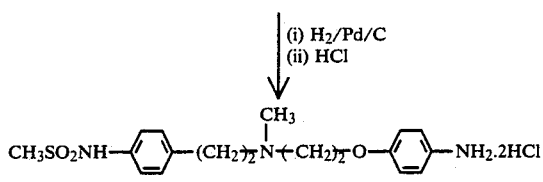

A solution of 1-(4-nitrophenoxy)-2-[N-methyl-N-(4-methanesulphonamidophenethyl)amino]ethane (1.0 g) in ethanol (50 ml) containing 5% Pd/C (0.1 g) was stirred under a hydrogen atmosphere (50 p.s.i.) for 4 hours. The reaction mixture was then filtered and the solvent evaporated to give a brown oil, which was purified by column chromatography on silica ("Kieselgel 60"-Trade Mark) eluting with methylene chloride. The appropriate fractions were combined and evaporated to give a yellow oil (0.5 g) which was dissolved in ethyl acetate and an ethereal solution of hydrochloric acid added until precipitation was complete. The resultant colourless solid was washed with dry ether to give the title compound, yield 0.35 g, m.p. 220°–223°.

Analysis %: Found: C,48.4; H,6.4; N,9.0; Calculated for $C_{18}H_{25}N_3O_3S.2HCl.\frac{1}{2}H_2O$: C,48.5; H,6.3; N,9.4

(C)
1-(4-Methanesulphonamidophenoxy)-2-[N-(4-methanesulphonamidophenethyl)-N-methylamino]ethane

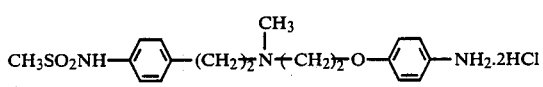

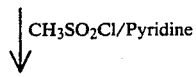

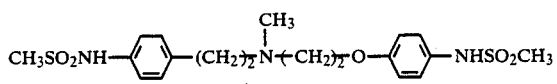

30

The title compound was prepared by mesylation of 1-(4-aminophenoxy)-2-[N-methyl-N-(4-methanesulphonamidophenethyl)amino]ethane dihydrochloride hemihydrate (95 mg) with mesyl chloride ir pyridine according to the procedure of Example 19(C), yield 30 mg, m.p. 147°–149°, confirmed spectroscopically to be identical to the product of Example 7(C).

Analysis %: Found: C,51.6; H,6.3; N,9.3; Calculated for $C_{19}H_{27}N_3O_5S_2$: C,51.9; H,6.15; N,9.4.

EXAMPLE 21
1-(4-Methanesulphonamidophenoxy)-2-[N-(4-methanesulphonamidophenethyl)-N-methylamino]ethane

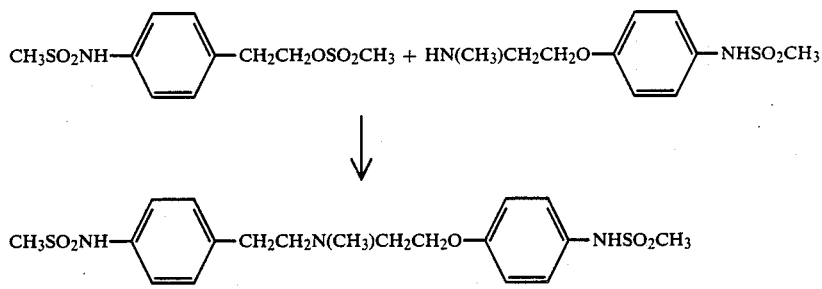

A solution of 4-[2-(methanesulphonyloxy)ethyl]methanesulphonanilide (0.3 g) and 4-[2-(methylamino)ethoxy]methanesulphonanilide (0.38 g) in ethanol (50 ml) was refluxed for 6 hours. On evaporation to dryness the residue was partitioned between 2N aqueous sodium bicarbonate solution and methylene chloride. After two further extractions with methylene chloride the organic portions were combined, washed with saturated brine, dried over magnesium sulphate, filtered and evaporated to dryness. The resultant brown oil was chromatographed on silica ("Kieselgel 60"-Trade Mark) eluting with methylene chloride followed by collection and evaporation of suitable fractions. The resultant colourless solid was crystallised from ethyl acetate to give the title compound, (0.21 g), m.p. 150°–152°, confirmed spectroscopically to be identical to the product of Example 7(C).

Analysis %: Found: C,51.6; H,6.3; N,9.3.; Calculated for $C_{19}C_{27}N_3O_5S_2$: C,51.9; H,6.15; N,9.4.

EXAMPLE 22
4-Methanesulphonamidophenoxy)-2-[N-(4-methanesulphonamidophenethyl)-N-methylamino]ethane

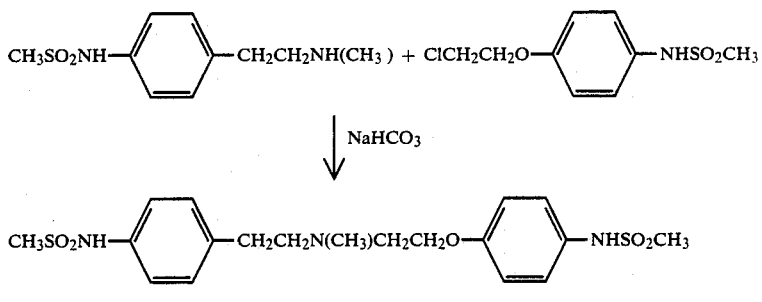

A mixture of 4-[2-methylamino)ethyl]methanesulphonanilide (0.49 g), 4-(2-chloroethoxy)methanesulphonanilide (0.5 g) and sodium bicarbonate (0.17 g) in ethanol (50 ml) was stirred at reflux for 3 days. On evaporation to dryness, the residue was partitioned between 2N aqueous sodium bicarbonate solution and methylene chloride. After two further extractions with methylene chloride the combined organic portions were washed with saturated brine, dried over anhydrous magnesium sulphate, filtered and evaporated to dryness. The resultant oil was chromatographed on silica ("Kieselgel 60"- Trade Mark) eluting with methylene chloride followed by collection and evaporation of suitable fractions. The resultant solid was crystallised from ethyl acetate to give the title compound, (0.25 g), m.p. 150°–152°, confirmed spectroscopically to be identical to the product of Example 7(C).

Analysis %: Found: C,52.3; H,6.3; N,9.2; Calculated for $C_{19}H_{27}N_3O_5S_2$: C,51.91 H,6.15; N,9.4.

EXAMPLE 23

(A) N,N-Bis-(4-nitrophenethyl)methylamine

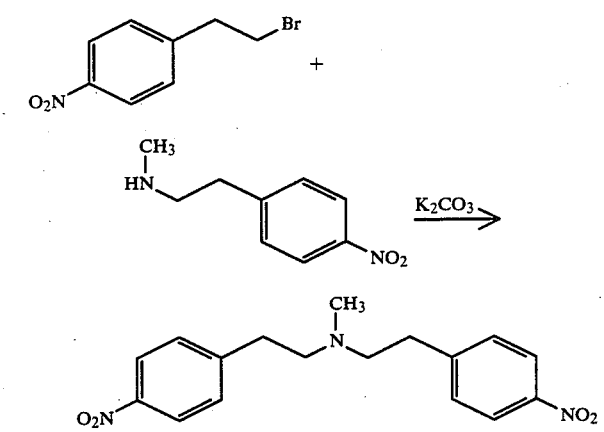

The title compound is a known compound having been isolated as a by-product (7%) from the reaction of 4-nitrostyrene and methylamine. [See Journal Organic Chemistry 1956 Vol. 21 p. 45.] However, it is preferred to make this compound by the route described below.

4-Nitrophenethyl bromide (2.6 g 11.3 mmol), N-methyl-4-nitrophenethylamine (2.0 g, 11.3 mmol) and potassium carbonate (1.6 g, 11.3 mmol) in acetonitrile were stirred at the reflux temperature for 4 days. The solvent was then removed and the residue was taken up in ethyl acetate, washed three times with aqueous sodium carbonate and three times with brine, dried (MgSO$_4$) and evaporated. The resultant oil was chromatographed on silica eluting with methylene chloride containing methanol (0% up to 2%). The appropriate fractions were combined and evaporated to give an orange oil which was triturated with hexane to give an orange powder which was filtered and dried, yield of the title compound, 1.3 g, m.p. 70°–71°.

Analysis %: Found: C,61.7; H,5.75; N,12.5; Calculated for $C_{17}H_{19}N_3O_4$: C,62.0; H,5.8; N,12.8.

Alternative preparation of N,N-bis-(4-nitrophenethyl)methylamine

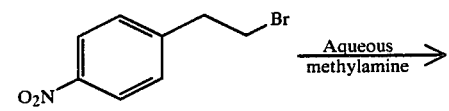

-continued

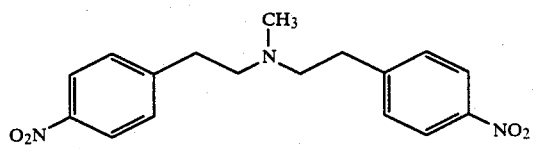

4-Nitrophenethyl bromide (I.0 g, 4.35 mmol) and 33% methylamine in water (10 ml) were stirred together at 55° for 2 hours. The reaction mixture was cooled and the resulting precipitate was collected by filtration and purified by column chromatography on silica eluting with methylene chloride containing methanol (0% up to 5%). The appropriate fractions were combined and evaporated to give the title compound, yield 0.19 g, m.p. 73°–75°.

Analysis %: Found: C,62.2; H,5.9; N,12.6. alculated for $C_{17}H_{19}N_3O_4$: C,62.0; H,5.8; N,12.8.

(B) N,N-Bis(4-aminophenethyl)methylamine

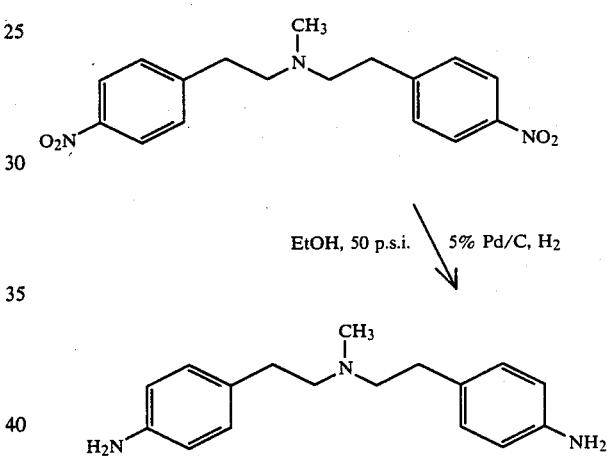

A solution of N,N-bis-(4-nitrophenethyl)methylamine (1.2 g, 3.6 mmol) in ethanol (50 ml) containing 5% Pd/C (0.15 g) was stirred under a hydrogen atmosphere (50 p.s.i.) for 4 hours. The reaction mixture was filtered and the solvent evaporated to give the title compound as an oil, yield 1.0 g, which was used directly without further purification.

N.M.R. (CDCl$_3$), δ=6.7 (q, 8H); 3.4 (br s, 4H); 2.6 (s, 8H); 2.3 (s, 3H).

(C) N,N-Bis-(4-methanesulphonamidophenethyl)methylamine

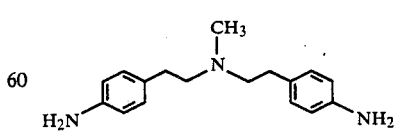

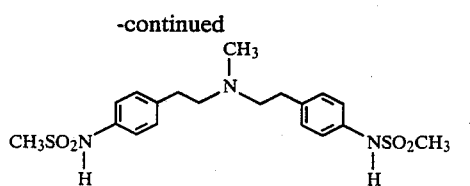

Methanesulphonic anhydride (1.29 g, 7.4 mmole) was added to a solution of N,N-bis-(4-aminophenethyl)methylamine (1.0 g, 3.7 mmole) and triethylamine (1 ml, 7.4 mmole) in dry methylene choride (50 ml) and stirred at room temperature for 2 hours. Methanesulphonic anhydride (1.29 g, 7.4 mmole) was added and the reaction mixture was stirred for a further 2 hours. The solvent was removed and the residue was taken up in methylene chloride, washed three times with aqueous sodium bicarbonate and three times with brine, dried (MgSO4), and evaporated. The resultant oil was chromatographed on silica eluting with methylene chloride containing methanol (0% up to 5%), which after combination and evaporation of the appropriate fractions, gave the title compound, yield 0.29 g, m.p. 170°–171°.

Analysis %: Found: C,53.15; N,6.5; H,9.7; Calculated for $C_{19}H_{27}N_3O_4 S_2$: C,53.6; N,6.4; H,9.8*.

*The sample contained a trace of methylene chloride (1/20 mole CH2Cl2 as adjudged by 'H-n.m.r. spectroscopy).

N.M.R. (TFAD), δ=7.1 (q, 8H); 3.5 (m, 4H);3.3 (m, 4H); 3.0 (s, 6H); 2.95 (s, 3H).

EXAMPLE 24

(A) N-(4-Nitrophenethyl)-4-nitrophenethylamine

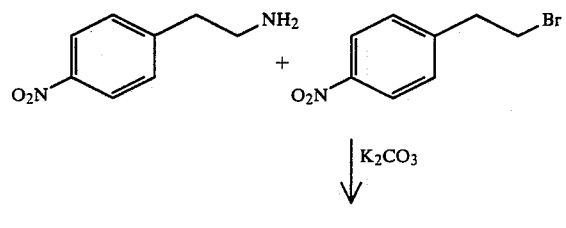

4-Nitrophenethylamine (4 g), 4-nitrophenethyl bromide (5.54 g) and potassium carbonate (3.32 g) were heated under reflux in acetonitrile (50 ml) for 2 days. The solvent was then evaporated, the residue taken up in ethyl acetate and washed three times with aqueous sodium carbonate and three times with brine. The organic phase was dried (Na2SO4), filtered and evaporated, and the residual oil was purified by chromatography on silica eluting with methylene chloride containing methanol (0% up to 5%). The product-containing fractions were combined and the solvent evaporated to give a solid which was recrystallised from ethyl acetate/hexane to give the title compound, yield 2.0 g, m.p. 86°–91°.

Analysis %: Found: C,60.7; H,5.6; N,13.1; Calculated for $C_{16}H_{17}N_3O_4$: C,60.9; H, 5.4; N,13.3.

(B) N,N-Bis-(4-nitrophenethyl)ethylamine

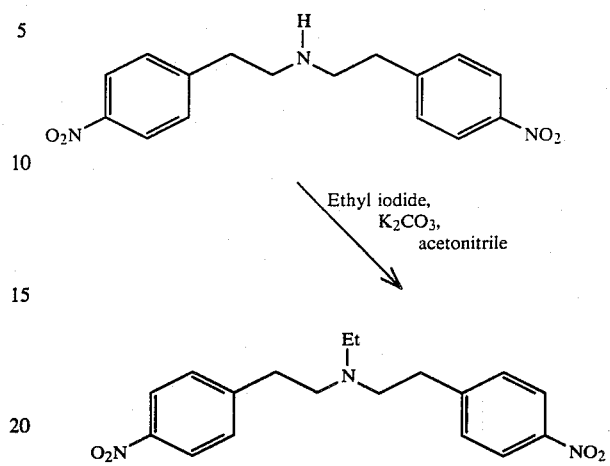

Ethyl iodide (0.37 g) was added dropwise to the product of part (A) (0.75 g) and potassium carbonate (0.33 g) in acetonitrile (20 ml) and the reaction mixture was heated under reflux for 18 hours. The reaction mixture was then evaporated to dryness and the residue taken up in methylene chloride, washed twice with aqueous sodium carbonate, twice with brine, then dried (Na2SO4), filtered and evaporated to dryness. The resulting oil was purified by column chromatography on silica eluting with methylene chloride containing methanol (0% up to 2%). The product-containing fractions were combined and evaporated to dryness to give the title compound as an oil, yield 0.47 g.

Analysis %: Found: C,62.7; H,6.0; N,12.7; Calculated for $C_{18}H_{21}N_3O_4$: C,63.0; H,6.2; N,12.2.

(C) N,N-Bis-(4-aminophenethyl)ethylamine

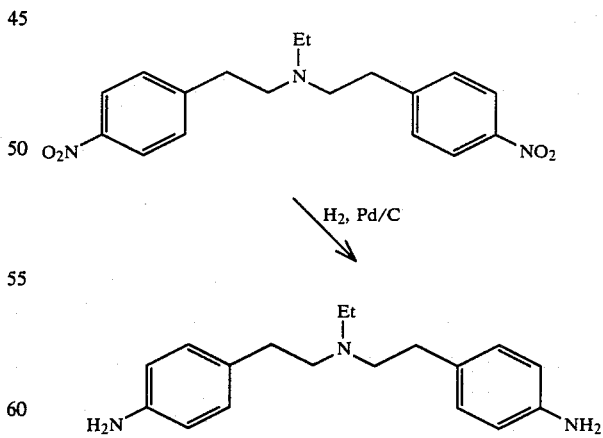

N,N-Bis-(4-nitrophenethyl)ethylamine (0.45 g) was reduced using H2/Pd/C in a similar fashion to Example 23(B) to provide the title compound, yield 0.32 g.

N.m.r. (CDCl3) δ=7.05 (d, 2H); 6.7 (d, 2); 3.55 (broad s, 4H); 2.70 (m, 10H); 1.1 (t, 3H).

(D)
N,N-Bis-(4-methanesulphonamidophenethyl)ethylamine

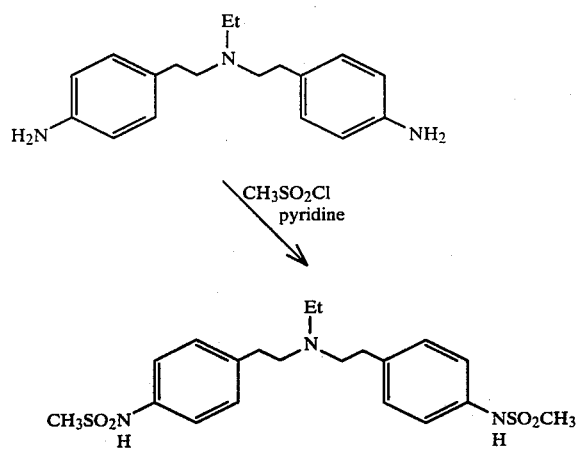

N,N-Bis-(4-aminophenethyl)ethylamine (0.3 g) was acylated with methanesulphonyl chloride in a similar fashion to Example 19(C) to produce the title compound as a foam, yield 0.12 g, m.p. <60°.

Analysis %: Found: C,54.1; H,6.8; N,9.2; Calculated for $C_{20}H_{29}N_3O_4S_2.\frac{1}{4}H_2O$: C,54.1; H,6.7; N,9.5.

The following Preparations, in which all temperatures are in °C., illustrate the preparation of certain novel starting materials, some of which also form a part of the invention:

Preparation 1

3-(2-Chloroethoxy)benzamide

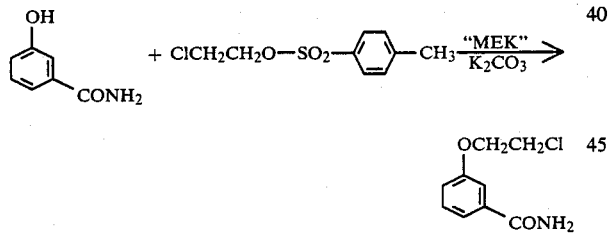

To a solution of 3-hydroxybenzamide (21.6 g) in methyl ethyl ketone ("MEK") was added 2-chloroethyl p-toluenesulphonate (55.46 g) and potassium carbonate (16.0 g). After stirring at reflux for 6 hours, the resultant mixture was poured onto water and a colourless solid filtered off. Crystallisation from ethanol gave the title compound, (22.2 g), m.p. 125°–126°.

Analysis %: Found: C,53.7; H,5.3; N,6.9; Calculated for $C_9H_{10}ClNO_2$: C,54.1; H,5.05; N,7.0.

Preparation 2

2-(2Chloroethoxy)-5-methyl benazamide

The title compound was made similarly to Preparation 1 from corresponding starting materials, m.p. 111°–113°.

Analysis %: Found: C,56.4; H,5.65; N,6.3; Calculated for $C_{13}H_{16}ClNO_3$: C,56.2; H,5.7; N,6.6.

Preparation 3

4-}4-[2Chloroethoxy]benzoyl≡morpholine

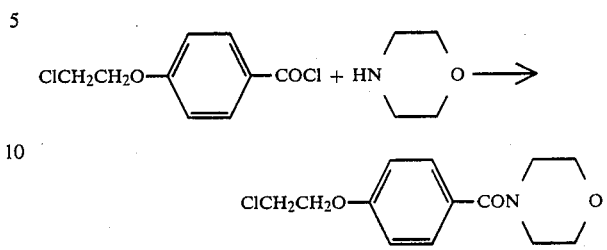

4-(2-Chloroethoxy)benzoyl chloride (5.0 g) was dissolved in dry methylene chloride and stirred while cooling to 0°. Morpholine (4.0 g) was added dropwise and the mixture was stirred at room temperature for 2 days. The resultant colourless solid was filtered off and the liquors allowed to stand from which the title compound crystallised (5.5 g), m.p. 102-4°.

Analysis %: Found: C,58.1; 1 H,6.0;N,5.25; Calculated for $C_{13}H_{16}ClNO_3$: C,57.9;H,6.0; N,5.2.

Preparation 4

N,N-Diethyl 4-(2-chloroethoxy)benzamide

The title compound was prepared similarly to the previous Preparation from corresponding starting materials, m.p. 80°-81°.

Analysis %: Found: C,60.8; H,7.0; N,5.3; Calculated for $C_{12}H_{18}ClNO_2$: C,61.05; H,7.1; N,5.5.

Preparation 5

5-Methyl-2-nitrophenyl 2'-bromoethyl ether

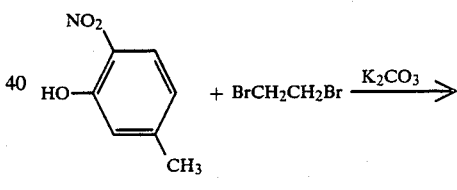

5-Methyl-2-nitrophenol (5.0 g) and potassium carbonate (4.6 g) in butanone (100 ml) were stirred together at room temperature for 0.5 hours. 1,2-Dibromoethane (3.1 g) was then added and the mixture stirred at reflux for 2 days. After evaporation to dryness, distilled water was added and the mixture was extracted three times with methylene chloride. The combined organic liquors were washed with water, dried over magnesium sulphate, filtered and evaporated to give a yellow solid which was removed by filtration and the solution was evaporated to low bulk giving the title compound as colourless crystals, m.p. 48°–49°, used in Example 10.

N.m.r. (CDCl$_3$), ppm δ=7.8 (d, 1H); 6.9 (m, 2H); 4.42 (t, 2H); 3.7 (t, 2H); 2.45 (s, 3H).

3-Nitrophenyl 2'-bromoethyl ether and 2-nitrophenyl 2'-bromoethyl ether used, respectively, as starting materials in Examples 8 and 9 are known compounds [see J. Med. Chem., (1970), 13(6), 1149 and C.A., 61, 601a].

Preparation 6

(A)

1-[N-Methyl-N-(4-nitrophenethyl)amino]-2-hydroxypropane

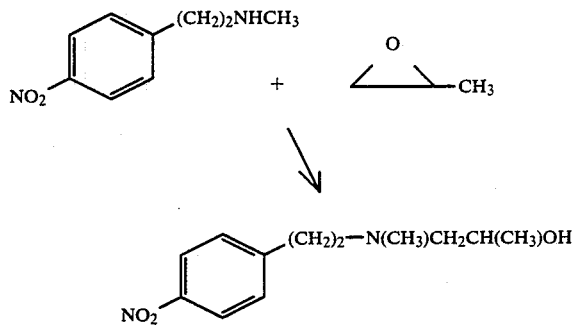

A solution of N-methyl-4-nitrophenethylamine (1.8 g) and propylene oxide (0.66 g) in ethanol (50 ml) was stirred at reflux for 5 hours. After evaporation to dryness the residual orange oil was chromatographed on silica ("Kieselgel 60"- Trade Mark) eluting with ethyl acetate followed by collection and evaporation of suitable fractions to give the title compound as a yellow oil.

N.m.r. (CDCl$_3$) p.p.m., $\delta=1.1$ (d, 3H); 2.3 (m, 2H); 2.32 (s, 3H); 2.75 (m, 2H); 2.9 (m, 2H); 3.15 (broad, 1H); 3.72 (m, 1H); 7.15 (d, 2H); 8.18 (d, 2H), (B)

1-[N-Methyl-N-(4-nitrophenethyl)amino]-2-chloropropane

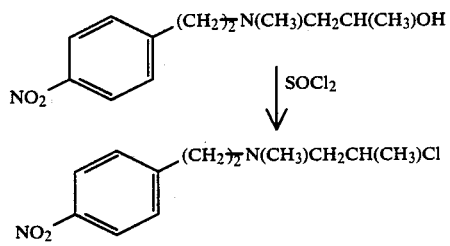

Thionyl chloride (50 ml) was added dropwise with stirring and cooling in an ice/water bath to 1-(N-methyl-N-(4-nitrophenethyl)amino)-2-hydroxypropane (1.5 g). After stirring at room temperature for 1 hour, the solution was refluxed on a steam bath for a further 2 hours. The solution was evaporated to dryness and the residual oil partitioned between 2N aqueous sodium carbonate solution and ethyl acetate. After two further extractions with ethyl acetate, the organic portions were combined, washed with a saturated brine solution, dried over anhydrous magnesium sulphate, filtered and evaporated to dryness. The resultant brown oil was chromatographed on silica ("Kieselgel 60"- Trade Mark) eluting with ethyl acetate followed by collection and evaporation of suitable fractions to give the title compound as a yellow oil, (0.75 g).

N.m.r. (CDCl$_3$), p.p.m. $\delta=1.48$ (d, 3H); 2.35 (s, 3H); 2.75 (m, 6H); 4.02 (q, 1H); 7.4 (d, 2H); 8.18 (d, 2H).

(C)

1-[N-methyl-N-(4-nitrophenethyl)amino]-2-(4-nitrophenoxy)propane and
2-[N-methyl-N-(4-nitrophenethyl)amino]-1-(4-nitrophenoxy)propane

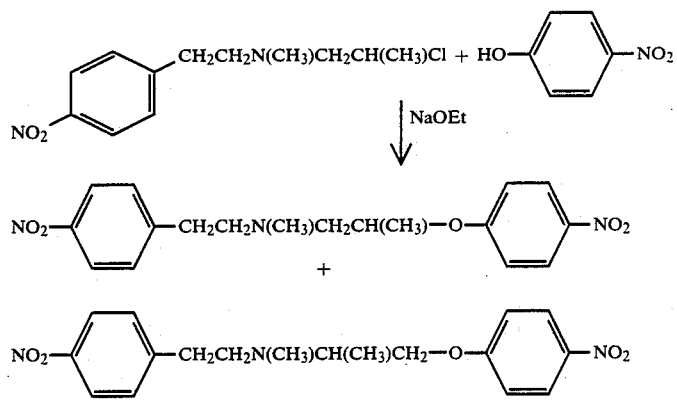

To a solution of sodium (0.075 g) in ethanol (50 ml) was added 4-nitrophenol (0.41 g) and the solution was stirred at room temperature for 1 hour. 1-[N-Methyl-N-(4-nitrophenethyl)amino]2-chloropropane (0.75 g) was added and the solution stirred at reflux for 3 days. The solution was then evaporated to dryness and the residual oil partitioned between water and methylene chloride. After two further extractions with methylene chloride, the organic portions were combined, washed with a saturated bring solution, dried over anhydrous magnesium sulphate, filtered and evaporated to dryness. The resultant orange oil (1.0 g) was chromatographed on silica ("Kieselgel 60"- Trade Mark) eluting with 1:1 hexane:ethyl acetate.

Collection and evaporation of the least polar product fractions gave the first-named title compound as a yellow oil, (0.25 g).

N.m.r. (CDCl$_3$) p.p.m.: $\delta=1.3$ (d, 3H); 2.4 (s, 3H); 2.75 (m, 6H); 4.58 (q, 1H); 6.91 (d, 2H); 7.35 (d, 2H); 8.1 (d, 2H); 8.2 (d, 2H).

Collection and evaporation of the more polar product fractions gave the second-named title compound as a yellow solid, (0.3 g), which was again characterised by n.m.r. spectroscopy.

N.m.r. (CDCl$_3$) p.p.m.: $\delta=1.1$ (d, 3H); 2.4s, 3H); 2.85 (m,4H); 3.2 (q, 1H); 3.95 (m, 2H); 6.92 (d, 2H); 7.35 (d, 2H); 8.2 (d, 2H); 8.2 (d, 2H).

Preparation 7

4-[2-(Methanesulphonylox)]ethyl]methanesulphonanilide

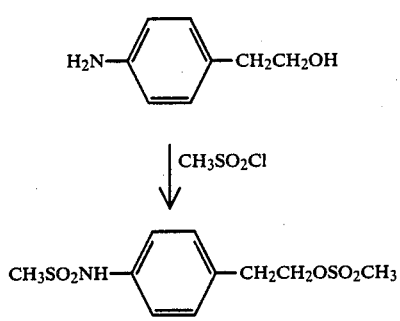

Methanesulphonyl chloride (50 ml) was added dropwise over 0.5 hours to a stirred solution of 4-aminophenethyl alcohol (41.15 g) in pyridine (350 ml) at 0°. The mixture was allowed to warm to room temperature and stirred overnight. The mixture was then poured onto water (700 ml) from which an orange solid crystallised. After filtration, the solid was dissolved in methylene chloride, dried over magnesium sulphate, filtered and the filtrate re-evaporated. Crystallisation of the resultant solid from ethyl acetate gave th title compound, (45.5 g), m.p. 136°-137°.

Analysis %; Found: C,40.6; H,5.2; N,4.9; Calculated for $C_{10}H_{15}NO_5S_2$: C,40.9; H,5.15; N,4.8.

Preparation 8

4-[2-(Methylamino)ethyl]methanesulphonanilide

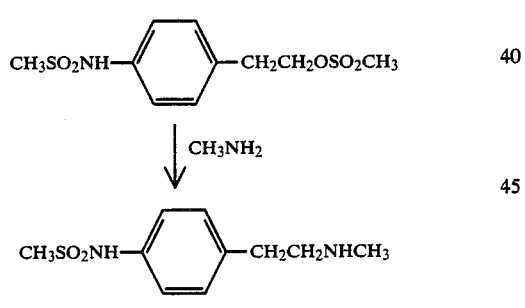

To a solution of 4-[2-(methanesulphonyloxy)ethyl]-methanesulphonanilide (10.3 g) in ethanol (20 ml) was added a solution of methylamine in industrial methylated spirits (30 ml of 33% solution). The mixture was heated with stirring at 85° in a pressure vessel for 17 hours. After cooling, the resultant solution was evaporated to dryness, the residue dissolved in water, and the resultant solution basified by the addition of sodium hydroxide (1.4 g) in water (12 ml). Evaporation gave an off-white solid which was chromatographed on silica ("Kieselgel "- Trade Mark) eluting with methylene chloride/methanol (3:1). Collection and evaporation of suitable fractions gave an off-white solid (4.8 g) which crystallised from ethyl acetate/methanol to give the title compound, (1.8 g), m.p. 133°-135°.

Analysis %: Found: C,52.5; H,7.1; N,12.2; Calculated for $C_{10}H_{16}N_2O_2S$: C,52.6; H,7.1; N,12.3.

Preparation 9

4-(2-Chloroethoxy)methanesulphonanilide

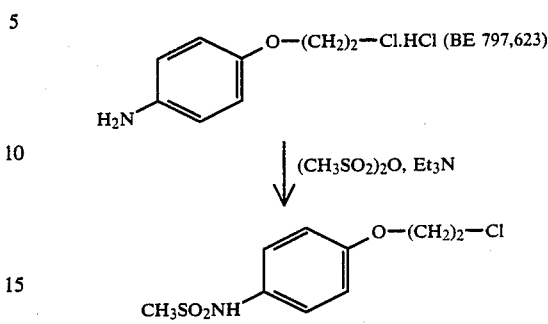

To a solution of 4-(2-chloroethoxy)aniline hydrochloride (9.5 g) and methanesulphonic anhydride (12.0 g) in methylene chloride (100 ml) was added dropwise with cooling, triethylamine (25 ml) and the mixture was stirred at room temperature overnight. The resultant mixture was partitioned between 2N aqueous sodium bicarbonate solution and methylene chloride. After two further extractions with methylene chloride, the organic portions were combined, dried over magnesium sulphate, filtered and evaporated to dryness. The resultant solid (9.5 g) was crystallised from methanol after filtration of impurity to give the title compound as slightly pink crystals, (5.6 g), m.p. 111°-114°.

N.m.r. (CDCl$_3$) p.p.m.: δ=2.84 (s, 3H); 3.8 (t, 2H); 4.2 (t, 2H); 6.75 (d, 2H); 7.15 (d, 2H); 9.0 (broad s, 1H).

Preparation 10

4-[2-(Methylaminoethoxy)]methanesulphonanilide hydrochloride

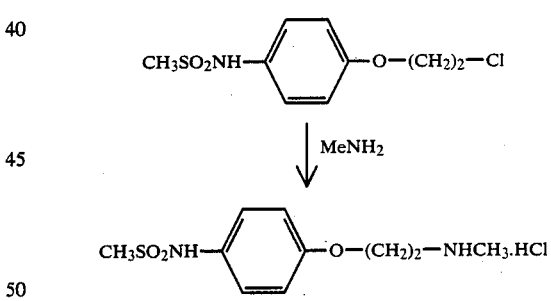

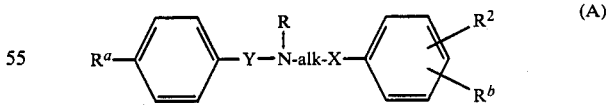

A suspension of 4-(2-chloroethoxy)methanesulphonanilide (12.7 g) in a solution of methylamine in industrial methylated spirits (160 ml of 33%) was heated with stirring at 100° in a pressure vessel overnight. After cooling the resultant dark solution was evaporated to dryness. Crystallisation of the residue from ethanol gave the title compound as a colourless solid, (10.1 g), m.p. 192°-194°.

Analysis %: Found: C,42.9; H,6.0; N,9.9; Calculated for $C_{10}H_{16}N_2O_3S.HCl$: C,42.8; H,6.1; N, 10.0.

Preparation 11

Methyl 4-(2-chloroethoxy)benzoate

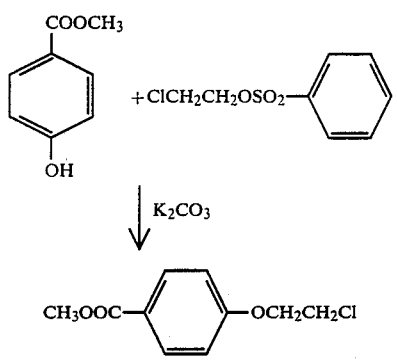

A mixture of methyl 4-hydroxybenzoate (15.2 g, 0.1 M), 2-(benzenesulphonyloxy)ethyl chloride (28.65 g, 0.12 M) and potassium carbonate (19.15 g, 0.1 M) in 4-methylpentan-2-one (170 ml) was stirred at reflux for 24 hours. After cooling, distilled water (170 ml) was added and the organic phase separated off. Evaporation to dryness gave a yellow solid which was crystallised from ethanol to give the title compound, yield (13.3 g), m.p. 56°–58°.

N.m.r. (CDCl$_3$) δ=8.02 (d, 2H); 6.96 (d, 2H); 4.3 (t, 2H); 3.92 (s, 3H); 3.88 (t, 2H).

Preparation 12

4-(2-Chloroethoxy)benzamide

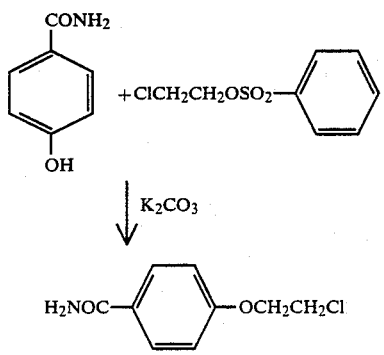

A mixture of 4-hydroxybenzamide (194 g, 1.25M), 2-(benzenesulphonyloxy)ethyl chloride (359 g, 1.8M), and potassium carbonate (172.8 g, 1.25M) in butan-2-one (2.16 l) was stirred at reflux for 24 hours. After cooling, distilled water (2.0 l) was added and the resultant precipitate filtered off, washed with water, and dried. Crystallisation from ethanol gave the title compound, yield (232.0 g), m.p. 66°.

Analysis %: Found: C,54.2; H,5.0; N,6.9; Calculated for C$_{10}$H$_{11}$ClO$_3$: C,54.25; H,5.1; N,7.0.

We claim:
1. A compound of the formula:

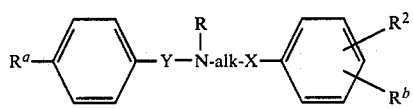

or a pharmaceutically acceptable salt thereof;

wherein
R$^a$ is —NO$_2$, —NH$_2$ or —NHSO$_2$R$^1$ where R$^1$ is a C$_1$–C$_4$ alkyl group;
R$^b$ is —NO$_2$, —NH$_2$ or R$^3$ where R$^3$ is —NHSO$_2$(-C$_1$–C$_4$ alkyl) or —CONR$^4$R$^5$ where R$^4$ and R$^5$ are each independently H or C$_1$–C$_4$ alkyl or together with the nitrogen atom to which they are attached represent a 1-pyrrolidinyl, piperidino, morpholino or N-methylpiperazin-1-yl group; with the proviso that when one of R$^a$ and R$^b$ is —NO$_2$, then the other is not —NH$_2$;
X is O or S absent;
Y is an ethylene group optionally substituted by a methyl group;
"alk" is an ethylene, trimethylene or tetramethylene group, "alk" being optionally substituted by a methyl group;
R is C$_1$–C$_4$ alkyl; and
R$^2$ is H, halo, CF$_3$ or C$_1$–C$_4$ alkyl.

2. A compound of the formula:

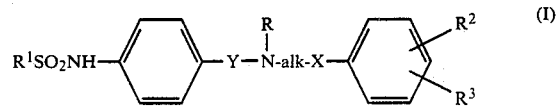

or a pharmaceutically acceptable salt thereof;

where
R and R$^1$ are each independently C$_1$–C$_4$ alkyl;
X is O or S absent;
Y is an ethylene group optionally substituted by a methyl group;
"alk" is an ethylene, trimethylene and tetramethylene group, "alk" being optionally substituted by a methyl group;
R$^2$ is H, halo, CF or C$_1$–C$_4$ alkyl; and
R$^3$ is a group of the formula —NHSO$_2$(C$_1$–C$_4$ alkyl) or —CONR$^4$R$^5$ where R$^4$ and R$^5$ are each independently H or C$_1$–C$_4$ alkyl or together with the nitrogen atom to which they are attached represent a 1-pyrrolidinyl, piperidino, morpholino or N-methylpiperazin-1-yl group.

3. A compound according to claim 2 wherein R$^1$ is methyl.
4. A compound according to claim 2 wherein R is methyl or ethyl.
5. A compound according to claim 3 wherein R is methyl or ethyl.
6. A compound according to claim 5 wherein R is methyl.
7. A compound according to claim 2 wherein X is O.
8. A compound according to claim 3 wherein X is O.
9. A compound according to claim 4 wherein X is O.
10. A compound according to claim 5 wherein X is O.
11. A compound according to claim 6 wherein X is O.
12. A compound according to claim 2 wherein Y is —(CH$_2$)$_2$—.
13. A compound according to claim 3 wherein Y is —(CH$_2$)$_2$—.
14. A compound according to claim 4 wherein Y is —(CH$_2$)$_2$—.
15. A compound according to claim 5 wherein Y is —(CH$_2$)$_2$—.
16. A compound according to claim 6 wherein Y is —(CH$_2$)$_2$—.
17. A compound according to claim 7 wherein Y is —(CH$_2$)$_2$—.

18. A compound according to claim 8 wherein Y is —(CH$_2$)$_2$—.

19. A compound according to claim 9 wherein Y is —(CH$_2$)$_2$—.

20. A compound according to claim 10 wherein Y is —(CH$_2$)$_2$—.

21. A compound according to claim 11 wherein Y is —(CH$_2$)$_2$—.

22. A compound according to claim 2 wherein R$^2$ is H, Cl or CH$_3$.

23. A compound according to claim 3 wherein R$^2$ is H, Cl or CH$_3$.

24. A compound according to claim 4 wherein R$^2$ is H, Cl or CH$_3$.

25. A compound according to claim 5 wherein R$^2$ is H, Cl or CH$_3$.

26. A compound according to claim 6 wherein R$^2$ is H, Cl or CH$_3$.

27. A compound according to claim 7 wherein R$^2$ is H, Cl or CH$_3$.

28. A compound according to claim 8 wherein R$^2$ is H, Cl or CH$_3$.

29. A compound according to claim 9 wherein R$^2$ is H, Cl or CH$_3$.

30. A compound according to claim 10 wherein R$^2$ is H, Cl or CH$_3$.

31. A compound according to claim 11 wherein R$^2$ is H, Cl or CH$_3$.

32. A compound according to claim 12 wherein R$^2$ is H, Cl or CH$_3$.

33. A compound according to claim 13 wherein R$^2$ is H, Cl or CH$_3$.

34. A compound according to claim 14 wherein R$^2$ is H, Cl or CH$_3$.

35. A compound according to claim 15 wherein R$^2$ is H, Cl or CH$_3$.

36. A compound according to claim 16 wherein R$^2$ is H, Cl or CH$_3$.

37. A compound according to claim 17 wherein R$^2$ is H, Cl or CH$_3$.

38. A compound according to claim 18 wherein R$^2$ is H, Cl or CH$_3$.

39. A compound according to claim 19 wherein R$^2$ is H, Cl or CH$_3$.

40. A compound according to claim 20 wherein R$^2$ is H, Cl or CH$_3$.

41. A compound according to claim 21 wherein R$^2$ is H, Cl or CH$_3$.

42. A compound according to claim 2 wherein R$^2$ is H.

43. A compound according to claim 2 wherein R$^3$ is NHSO$_2$CH$_3$, —CONH$_2$, CON(C$_2$H$_5$)$_2$ or

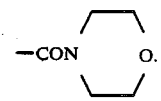

44. A compound according to claim 43 wherein R$^3$ is —NHSO$_2$CH$_3$.

45. A compound of the formula:

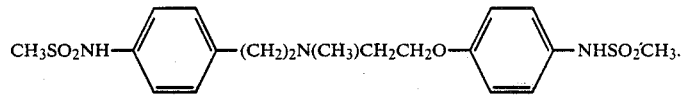

46. A compound according to claim 2 wherein Y is —(CH$_2$)$_2$—and X is O or S.

47. A pharmaceutical composition comprising an anti-arrhythmic effective amount of a compound of claim 2 in combination with a pharmaceutically acceptable diluent or carrier.

48. A method of treating cardiac arrhythmia comprising administering to an arrhythmic host in need of such treatment an anti-arrhythmic effective dose of a compound of claim 2 in combination with a pharmaceutically acceptable diluent or carrier.

* * * * *

UNITED STATES PATENT AND TRADEMARK OFFICE
Certificate

Patent No. 4,959,366                            Patented: September 25, 1990

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Peter E. Cross, New York, N.Y.; and Geoffrey N. Thomas, New York, N.Y.

Signed and Sealed this Eleventh Day of May, 1999.

JOHN KIGHT III
*Supervisory Patent Examiner*
Art Unit 1612

UNITED STATES PATENT AND TRADEMARK OFFICE
CERTIFICATE OF CORRECTION

PATENT NO. : 4,959,366
APPLICATION NO. : 07/044086
DATED : September 25, 1990
INVENTOR(S) : Cross et al.

It is certified that error appears in the above-identified patent and that said Letters Patent is hereby corrected as shown below:

In the attached Certificate Extending Patent Term Under 35 U.S.C. § 156, issued April 27, 2005:

(a) in the heading of the Certificate, following [(45) ISSUED], "May 25, 1990" should read --September 25, 1990--.

(b) in the heading of the Certificate, following [(95) PRODUCT], "TIKOSYN® (methanesulfonamide)" should read --TIKOSYN® (dofetilide)--.

(c) at lines 3-4 of the first paragraph of the text of the Certificate, "TIKOSYN® (methanesulfonamide)" should read --TIKOSYN® (dofetilide)--.

Signed and Sealed this

Twenty-fifth Day of November, 2008

JON W. DUDAS
*Director of the United States Patent and Trademark Office*

UNITED STATES PATENT AND TRADEMARK OFFICE

(12)  CERTIFICATE EXTENDING PATENT TERM
UNDER 35 U.S.C. § 156

| | | | |
|---|---|---|---|
| (68) | PATENT NO. | : | 4,959,366 |
| (45) | ISSUED | : | May 25, 1990 |
| (75) | INVENTOR | : | Cross, et al. |
| (73) | PATENT OWNER | : | Pfizer Inc. |
| (95) | PRODUCT | : | TIKOSYN® (methanesulfonamide) |

This is to certify that an application under 35 U.S.C. § 156 has been filed in the United States Patent and Trademark Office, requesting extension of the term of U.S. Patent No. 4,959,366 based upon the regulatory review of the product TIKOSYN® (methanesulfonamide) by the Food and Drug Administration. Since it appears that the requirements of the law have been met, this certificate extends the term of the patent for the period of

(94)   Five Years from September 25, 2007, the original expiration date of the patent, subject to the payment of maintenance fees as provided by law, with all rights pertaining thereto as provided by 35 U.S.C. § 156(b).

I have caused the seal of the United States Patent and Trademark Office to be affixed this 27th day of April 2005.

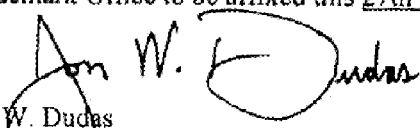

Jon W. Dudas
Under Secretary of Commerce for Intellectual Property and
  Director of the United States Patent and Trademark Office